United States Patent
Virdee et al.

(10) Patent No.: US 12,351,857 B2
(45) Date of Patent: Jul. 8, 2025

(54) ACTIVITY BASED PROBES

(71) Applicant: University of Dundee, Dundee (GB)

(72) Inventors: Satpal Virdee, Dundee (GB); Sunil Mathur, Dundee (GB); Adam Fletcher, Dundee (GB)

(73) Assignee: University of Dundee, Dundee (GB)

( * ) Notice: Subject to any disclaimer, the term of this patent is extended or adjusted under 35 U.S.C. 154(b) by 385 days.

(21) Appl. No.: 17/753,324

(22) PCT Filed: Aug. 28, 2020

(86) PCT No.: PCT/EP2020/074069
§ 371 (c)(1),
(2) Date: Feb. 28, 2022

(87) PCT Pub. No.: WO2021/038034
PCT Pub. Date: Mar. 4, 2021

(65) Prior Publication Data
US 2022/0267825 A1   Aug. 25, 2022

(30) Foreign Application Priority Data

Aug. 28, 2019 (GB) ........................ 1912339
Nov. 13, 2019 (GB) ........................ 1916504

(51) Int. Cl.
*C12Q 1/48* (2006.01)
*C12N 9/00* (2006.01)
*C12N 9/10* (2006.01)

(52) U.S. Cl.
CPC ............... *C12Q 1/48* (2013.01); *C12N 9/104* (2013.01); *G01N 2333/9108* (2013.01)

(58) Field of Classification Search
CPC . C12Q 1/48; C12N 9/104; C12N 9/93; C07K 2319/00; C07K 2319/21; C07K 2319/50; C07K 2319/60; C07K 14/4748; C07K 14/4702; C07K 14/47
See application file for complete search history.

(56) References Cited

U.S. PATENT DOCUMENTS

2018/0170878 A1   6/2018   Statsyuk et al.

FOREIGN PATENT DOCUMENTS

| WO | WO 2012/036551 A1 | 3/2012 |
| WO | WO 2016/051174 A1 | 4/2016 |

OTHER PUBLICATIONS

Liang J. et al., "Chemical Synthesis of Diubiquitin-Based Photoaffinity Probes for Selectively Profiling Ubiquitin-Binding Proteins", Angew. Chem. Int. Ed., 2017, 56, 2744-2748. (Year: 2017).*
Scott D.C. et al., "Structure of a Ring E3 Trapped in Action Reveals Ligation Mechanism for the Ubiquitin-like Protein NEDD8", Cell, 2014, vol. 157, pp. 1671-1684. (Year: 2014).*
Hewings DS, Flygare JA, Bogyo M, Wertz IE. Activity-based probes for the ubiquitin conjugation-deconjugation machinery: new chemistries, new tools, and new insights. FEBS J. May 2017;284(10):1555-1576. doi: 10.1111/febs.14039. Epub Mar. 10, 2017. PMID: 28196299; PMCID: PMC7163952.
Hu M, Li P, Li M, Li W, Yao T, Wu JW, Gu W, Cohen RE, Shi Y. Crystal structure of a UBP-family deubiquitinating enzyme in isolation and in complex with ubiquitin aldehyde. Cell. Dec. 27, 2002;111(7):1041-54. doi: 10.1016/s0092-8674(02)01199-6. PMID: 12507430.
Love KR, Pandya RK, Spooner E, Ploegh HL. Ubiquitin C-terminal electrophiles are activity-based probes for identification and mechanistic study of ubiquitin conjugating machinery. ACS Chem Biol. Apr. 17, 2009;4(4):275-87. doi: 10.1021/cb9000348. PMID: 19256548; PMCID: PMC2693349.
Mathur Sunil et al: "Photocrosslinking Activity-Based Probes for Ubiquitin Ring E3 Ligases", Cell Chemical Biology, vol. 27, No. 1, Dec. 16, 2019, p. 74, XP086020402, ISSN: 2451-9456, DOI: 10.1016/ J.CHEMBIOL.2019.11.013.
Mulder MP, Witting K, Berlin I, et al. A cascading activity-based probe sequentially targets E1-E2-E3 ubiquitin enzymes. Nature Chemical Biology. Jul. 2016;12(7):523-530. DOI: 10.1038/nchembio. 2084. PMID: 27182664; PMCID: PMC5108872.
Naito M, Ohoka N, Shibata N. Snipers-Hijacking IAP activity to induce protein degradation. Drug Discov Today Technol. Apr. 2019;31:35-42. doi: 10.1016/j.ddtec.2018.12.002. Epub Jan. 14, 2019. PMID: 31200857.
Niphakis MJ, Cravatt BF. Enzyme inhibitor discovery by activity-based protein profiling. Annu Rev Biochem. 2014;83:341-77. doi: 10.1146/annurev-biochem-060713-035708. PMID: 24905785.
Pao, KC., Stanley, M., Han, C. et al. Probes of ubiquitin E3 ligases enable systematic dissection of parkin activation. Nat Chem Biol 12, 324-331 (2016). https://doi.org/10.1038/nchembio.2045.
Robert Byrne et al:: "Activity-Based Probes for HECT E3 Ubiquitin Ligases", Chembiochem, vol. 18, No. 14, Jul. 18, 2017, pp. 1415-1427, XP055750985, ISSN: 1439-4227, DOI: 10.1002/cbic. 201700006.
Spradlin JN, Hu X, Ward CC, Brittain SM, Jones MD, Ou L, To M, Proudfoot A, Ornelas E, Woldegiorgis M, Olzmann JA, Bussiere DE, Thomas JR, Tallarico JA, McKenna JM, Schirle M, Maimone TJ, Nomura DK. Harnessing the anti-cancer natural product nimbolide for targeted protein degradation. Nat Chem Biol. Jul. 2019; 15(7):747-755. doi: 10.1038/s41589-019-0304-8. Epub Jun. 17, 2019. PMID: 31209351; PMCID: PMC6592714.
Ward CC, Kleinman JI, Brittain SM, Lee PS, Chung CYS, Kim K, Petri Y, Thomas JR, Tallarico JA, McKenna JM, Schirle M, Nomura DK. Covalent Ligand Screening Uncovers a RNF4 E3 Ligase Recruiter for Targeted Protein Degradation Applications. ACS Chem Biol. Nov. 15, 2019;14(11):2430-2440. doi: 10.1021/acschembio. 8b01083. Epub May 13, 2019. PMID: 31059647; PMCID: PMC7422721.
Witting Katharina F et al: "Advancing our Understanding of Ubiquitination Using the Uh-Toolkit", Journal of Molecular Biology, vol. 429, No. 22, Nov. 10, 2017 (Nov. 10, 2017), pp. 3388-3394, XP085271810, ISSN: 0022-2836, DOI: 10.1016/J.JMB.2017.04.002 abstract; Fig. 1, 2.

(Continued)

*Primary Examiner* — Satyendra K Singh
(74) *Attorney, Agent, or Firm* — Hoxie & Associates LLC

(57) ABSTRACT

The present invention is directed to the development of novel photocrosslinking activity based probes (ABPs) and their uses. Specifically, ubiquitin-charged E2 conjugating enzymes are engineered and shown to be effective ABPs of RING ubiquitin E1 and E3 ligases as well as deubiquitination enzymes.

18 Claims, 29 Drawing Sheets

Figure 1:
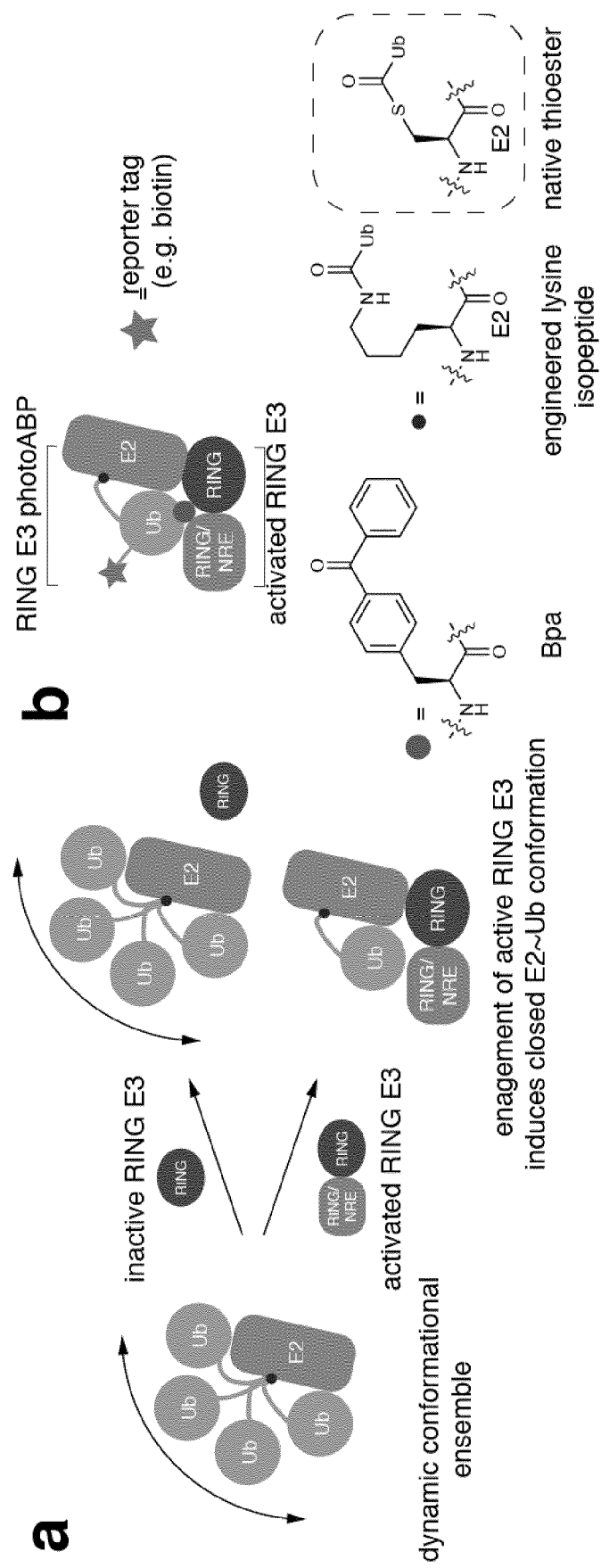
Figure 1:
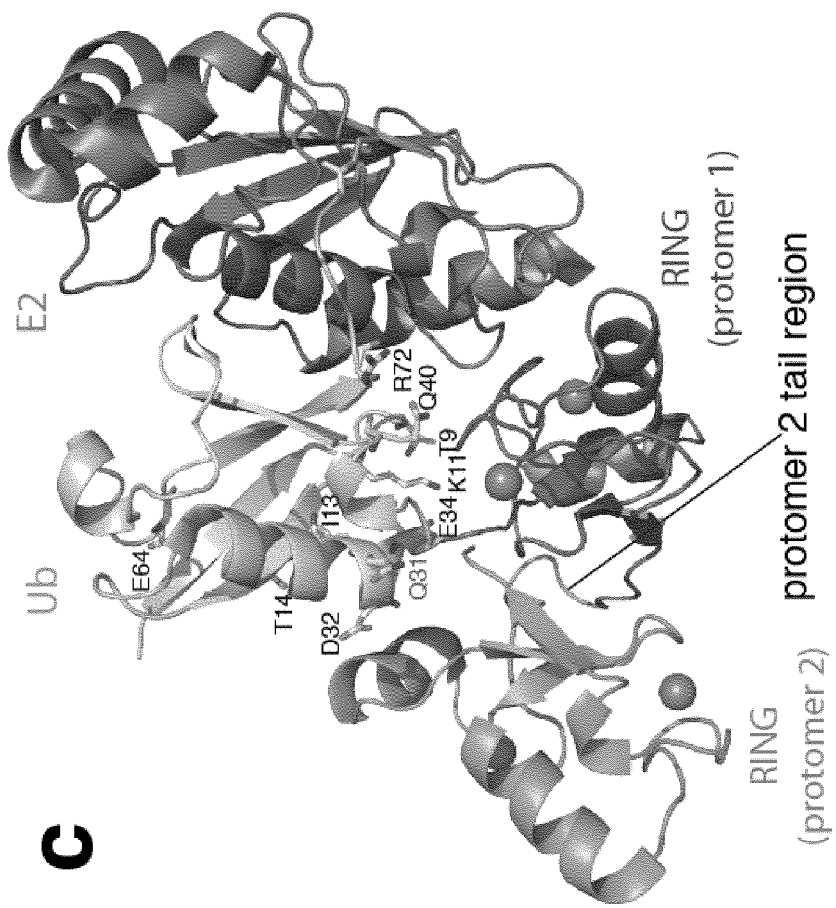
Figure 1:
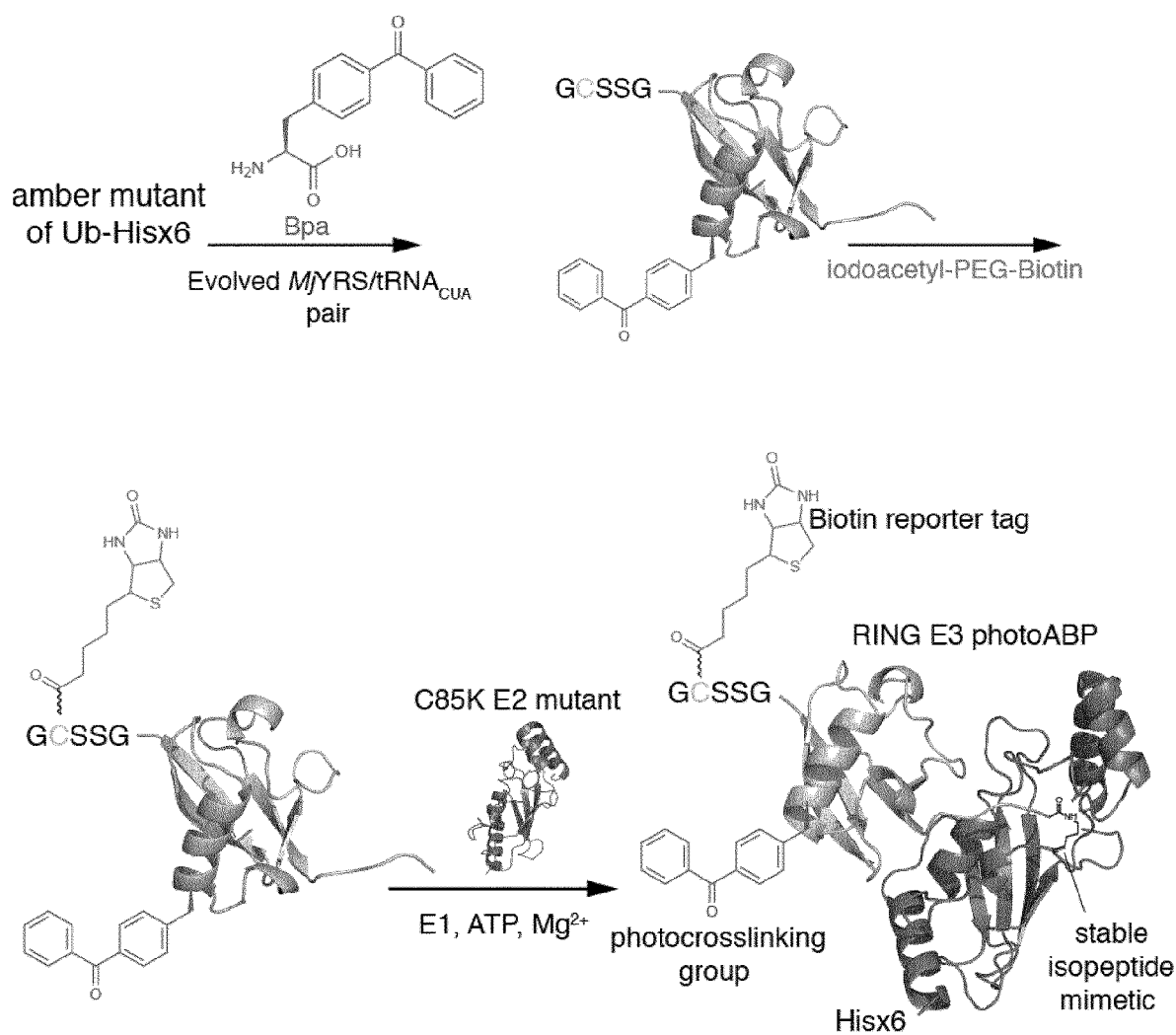

Specification includes a Sequence Listing.

(56) References Cited

OTHER PUBLICATIONS

Xu L, Fan J, Wang Y, Zhang Z, Fu Y, Li YM, Shi J. An activity-based probe developed by a sequential dehydroalanine formation strategy targets HECT E3 ubiquitin ligases. Chem Commun (Camb). Jun. 21, 2019;55(49):7109-7112. doi: 10.1039/c9cc03739j. Epub Jun. 3, 2019. PMID: 31157339.
Braxton et al., "Ubiquitin Chains Bearing Genetically Encoded Photo-Cross-Linkers Enable Efficient Covalent Capture of (Poly)ubiquitin-Binding Domains," Biochemistry, vol. 58, p. 883-886, (2019).
Yamano et al., "Site-specific Interaction Mapping of Phosphorylated Ubiquitin to Uncover Parkin Activation," The Journal of Biological Chemistry, vol. 290, No. 42, p. 25199-25211, (2015).

\* cited by examiner d

SEQUENCE LISTING

```
<160> NUMBER OF SEQ ID NOS: 2

<210> SEQ ID NO 1
<211> LENGTH: 76
<212> TYPE: PRT
<213> ORGANISM: Artificial Sequence
<220> FEATURE:
<223> OTHER INFORMATION: The sequence (activated ubiquitin comprising a
      photocrosslinker moiety) is synthesized.

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 6
<212> TYPE: PRT
<213> ORGANISM: Artificial Sequence
<220> FEATURE:
<223> OTHER INFORMATION: The sequence (terminal motif) is synthesized.

<400> SEQUENCE: 2

Met Gly Cys Ser Ser Gly
1               5
```

ACTIVITY BASED PROBES

CROSS REFERENCE TO RELATED APPLICATIONS

This application is a United States Application under 35 U.S.C. 371 claiming benefit of PCT Application No. PCT/EP2020/074069, filed on Aug. 28, 2020, which claims the benefit of United Kingdom Application No. 1912339.7, filed on Aug. 28, 2019 and United Kingdom Application No. 1916504.2, filed on Nov. 13, 2019, the contents of each of which are incorporated herein by reference.

FIELD OF THE INVENTION

The present invention is directed to the development of novel photocrosslinking activity based probes (ABPs) and their uses. Specifically, ubiquitin-charged E2 conjugating enzymes are engineered and shown to be effective ABPs of RING ubiquitin E1 and E3 ligases as well as deubiquitination enzymes.

BACKGROUND OF THE INVENTION

Activity-based protein profiling is an invaluable technique for studying enzyme biology and facilitating the development of therapeutics. Ubiquitin E3 ligases (E3s) are one of the largest enzyme families and regulate a host of (patho)physiological processes. The largest subtype are the RING E3s of which there are >600 members. RING E3s have adaptor-like activity that can be subject to diverse regulatory mechanisms and have become attractive drug targets. To the best of our knowledge, activity-based probes (ABPs) for measuring RING E3 activity do not exist.

Ubiquitination is a fundamental post-translational modification that regulates normal cellular physiology and its dysfunction can lead to disease onset (Rape, M. (2018). *Nat Rev Mol Cell Biol* 19, 59-70). Ubiquitination is carried out by an enzymatic cascade involving the sequential activities of ubiquitin E1 activating (E1), ubiquitin E2 conjugating (E2) and ubiquitin E3 ligases (E3s) (Hershko, A., and Ciechanover, A. (1998). *Annu Rev Biochem* 67, 425-479). Ubiquitin (Ub) is covalently transferred from catalytic cysteine in E1 onto catalytic cysteine in E2 forming a thioester-linked E2 intermediate (E2~Ub). Hundreds of E3s that recruit E2~Ub and ubiquitinate specific substrates are known to exist. Divergence of E3 mechanism has led to two general classes. "Cys E3s", of which there are ~50, utilize a catalytic cysteine to form a covalent thioester-linked intermediate with the Ub prior to substrate modification (K. C. Pao et al, *Nature*, 2018, 556, 381-385; Scheffner, M., Nuber, U., and Huibregtse, J. M. (1995). *Nature* 373, 81-83; Wenzel, D. M., et al. (2011), *Nature* 474, 105-108).

However, the largest class of E3s are adapter-like E3s of which there are >600 distinct forms (Deshaies, R. J., and Joazeiro, C. A. (2009). *Annu Rev Biochem* 78, 399-434). Adapter-like E3s are devoid of a catalytic nucleophile and catalyze direct transfer of Ub from E2~Ub to substrate. This adapter-like activity is utilized by multi-subunit Cullin-RING E3s and ~350 single polypeptide RING E3s (hereafter simply referred to as RING E3s). The latter can exist as monomers, homodimers or heterodimers (Metzger, M. B. et al. (2014). *Biochim Biophys Acta* 1843, 47-60). Activity regulation is a particularly important aspect of E3 biology that ensures cellular homeostasis and adaptive signaling. Dysregulation can lead to disease onset hence RING E3s have become attractive therapeutic targets (Burgess, A. et al. (2016). *Front Oncol* 6, 7). However, the cellular roles and the regulatory mechanisms for the vast majority of RING E3s remain poorly understood. Furthermore, RING E3s have recently been shown to be compatible with targeted protein degradation strategies (e.g. PROTAC methodology) (Naito, M., Ohoka, N., and Shibata, N. (2019). *Drug Discov Today Technol*, 31, 35-42; Spradlin, J. N. et al. (2019). *Nat Chem Biol* 15, 747-755; Ward, C. C. et al. (2019). ACS Chem Biol.). Tools for determining which RING E3s are active in clinical contexts are needed to further leverage this potential.

A hallmark of adapter-like E3s is that when in the active state, they shift the dynamic E2~Ub conformational ensemble towards a distinct population where the E2~Ub conjugate adopts a folded back or "closed" conformation (Dou, H. et al. (2012b). *Nat Struct Mol Biol*, 19, 876-883; Plechanovova, A. et al. (2012). *Nature* 489, 115-120; Pruneda, J. N. et al. (2012). *Mol Cell*, 47, 933-942; Pruneda, J. N. et al. (2011). Biochemistry 50, 1624-1633; see FIG. 1a). This conformation activates the thioester bond within E2~Ub to nucleophilic attack and is a requisite for efficient aminolysis activity. RING E3 activity can be regulated and switching to an activated state is achieved by the E3 acquiring structural features that engage the Ub component thereby promoting induction of the closed conformation. For example, RING E3s such as RNF4 and BIRC7 are activated by RING domain dimerization where a tail region of the second RING protomer engages the Ub component (Dou, H. et al, 2012b; Plechanovova, A. et al., 2012, supra). Dimerization can be regulated by cellular signals and in the case of RNF4, this is brought about by binding to poly-SUMO chains (Rojas-Fernandez, A. et al. (2014). *Mol Cell*, 53, 880-892).

For activation of monomeric RING E3s a so-called non-RING element has been shown to play a role in binding the Ub component and in the case of Cbl-b and c-Cbl, this is a phosphorylated tyrosine residue (Dou, H. et al. (2013). *Nat Struct Mol Biol*, 20, 982-986). Phosphorylation is carried out by the kinase c-Src in response to growth factor stimulation and Cbl activation triggers the ubiquitination and degradation of receptor and non-receptor tyrosine kinases. RING E3s that require dimerization and the presence of a non-RING element have also been reported (Koliopoulos, M. G. et al. (2016). *EMBO J*, 35, 1204-1218). Additional RING E3 activation mechanisms exist including allosteric binding of accessory proteins or ligands (DaRosa, P. A. et al. (2015). *Nature*, 517, 223-226; Dickson, C. et al. (2018). *Elife*, 7; Duda, D. M. et al. (2012). *Mol Cell*, 47, 371-382; Wright, J. D., Mace, P. D., and Day, C. L. (2016). *Nat Struct Mol Biol*, 23, 45-52). Numerous crystal structures of E2~Ub bound to activated RING E3s have been solved revealing a highly conserved binding mode (Dou, H. et al. 2012b and 2013; Koliopoulos, M. G. et al, 2016; Plechanovova, A. et al., 2012; Wright, J. D., Mace, P. D., and Day, C. L., 2016, supra). Importantly, a consensus region of the Ub component in the closed E2~Ub conjugate becomes proximal to the activated RING. Furthermore, biophysical analysis demonstrates that activated RING E3s studied thus far can have higher free energy of binding for E2~Ub than their inactive forms (Berndsen, C. E. et al. (2013). *Nat Chem Biol.* 9, 154-156; Buetow, L. et al. (2016). *BMC Biol.* 14, 76).

Activity-based probes (ABPs) are powerful chemical tools that undergo activity-dependent covalent labelling of enzyme family members (Hewings, D. S. et al. (2017). *FEBS J.*, 284, 1555-1576; Niphakis, M. J., and Cravatt, B. F. (2014). *Annu Rev Biochem.*, 83, 341-377). This enables: (i) the study of enzyme regulation, (ii) discovery of novel enzyme classes, (iii) inhibitor screening, (iv) inhibitor selectivity profiling (v) stabilization of enzymatic intermediates for structural studies (Hu, M. et al. (2002). *Cell*, 111, 1041-1054). We and others have developed ABPs for Cys E3s which have been deployed to dissect E3 activation mechanisms and discover entirely novel E3 classes (Love, K. R. et al. (2009). *ACS Chem. Biol.*, 4, 275-287; Mulder, M. P. et al. (2016). *Nat. Chem. Biol.*, 12, 523-530; Pao, K. C. et al. (2016). *Nat. Chem. Biol.*, 12, 324-331; Xu, L. et al. (2019). *Chem. Commun. (Camb)*, 55, 7109-7112).

To the best of the inventors' knowledge, ABPs that assess RING E3 ligase activity do not currently exist. The current invention aims to address this by providing ABPs that assess RING E3 ligase.

SUMMARY OF THE INVENTION

Without being bound by theory, the inventors consider that the conserved (and activity-dependent) consensus interaction of the Ub component within a closed E2~Ub, coupled with the enhanced free energy of binding for activated RING E3s, could be exploited for the development of ABPs.

ABPs based on an engineered ubiquitin molecule are disclosed herein. It has been found that activated ubiquitin molecules comprising a photocrosslinker moiety in place of a glutamine residue at position 31 and/or an aspartic acid residue at position 32 of ubiquitin are surprisingly effective as ABPs when conjugated to an E2 conjugating enzyme. Such ABPs are effective in activity profiling RING E3 ligases in diverse sample types and may be useful for the study of RING E3 regulation, target discovery, biomarker applications, modulator discovery and structural studies, for example.

Therefore, in a first aspect, the invention provides an activated ubiquitin molecule comprising a photocrosslinker moiety in place of a glutamine residue at position 31 and/or an aspartic acid residue at position 32 of ubiquitin.

In a second aspect, the invention provides a conjugate molecule comprising the activated molecule of the first aspect conjugated to an E2 conjugating enzyme.

In a third aspect, the invention provides use of the conjugated molecule of the second aspect in a method of activity profiling RING E3 enzymes, RING E1 enzymes and/or deubiquitinating enzymes.

In a fourth aspect, the invention provides a method of detecting an interaction between the conjugate molecule of the second aspect and a RING E3 enzyme, RING E1 enzyme and/or deubiquitinating enzyme, the method comprising contacting the conjugate molecule of the second aspect with said RING E3 enzyme, RING E1 enzyme and/or deubiquitinating enzyme and detecting the formation of any new conjugates. For example, by appending an enrichable reporter group to the conjugate such as biotin, activated RING E3s can be enriched from native cells and identified by mass spectrometry.

The skilled person is aware that any reference to an aspect of the invention includes every embodiment of that aspect. For example, any reference to the first aspect of the invention includes the first aspect and all embodiments of the first aspect.

LIST OF FIGURES

FIG. 1: Strategy and synthetic scheme for production of photocrosslinking ABPs for RING E3 ligases. a) Binding of activated RING E3 induces closed conformation of otherwise conformationally dynamic E2~Ub conjugate. Activation can be achieved by RING dimerization whereas monomeric RING E3s can be activated by the presence of a non-RING element (NRE). The Ub component of E2~Ub interacts with RING/NRE region. b) Judicious incorporation of a p-benzoyl-L-phenyl alanine (Bpa) crosslinking amino acid within a stabilized E2~Ub conjugate serves as an ABP for RING E3 activity. c) Crystal structure of E2~Ub in complex with activated, dimeric RING E3 (RNF4). Ten amino acid sites within Ub that are proximal to the activated E3 were tested for Bpa incorporation. The Q31 was found to be optimal. d) Synthetic scheme for photocrosslinking ABP.

Figure 2:
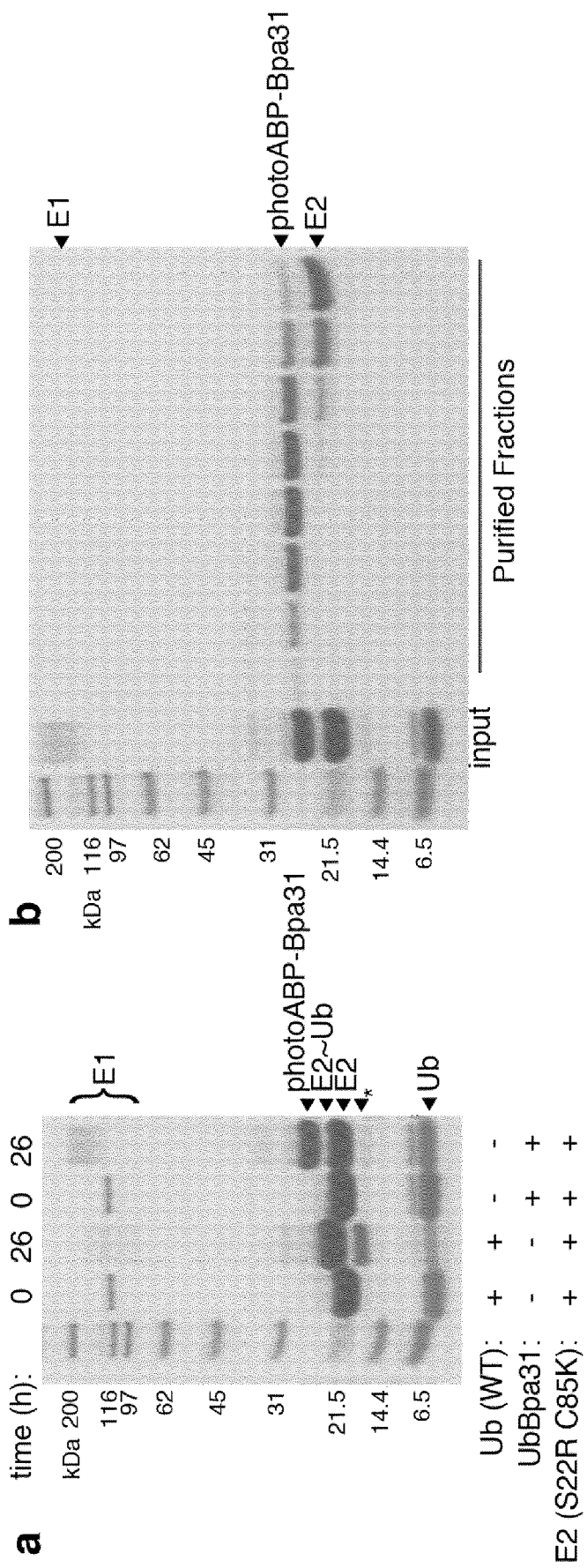
Figure 2:
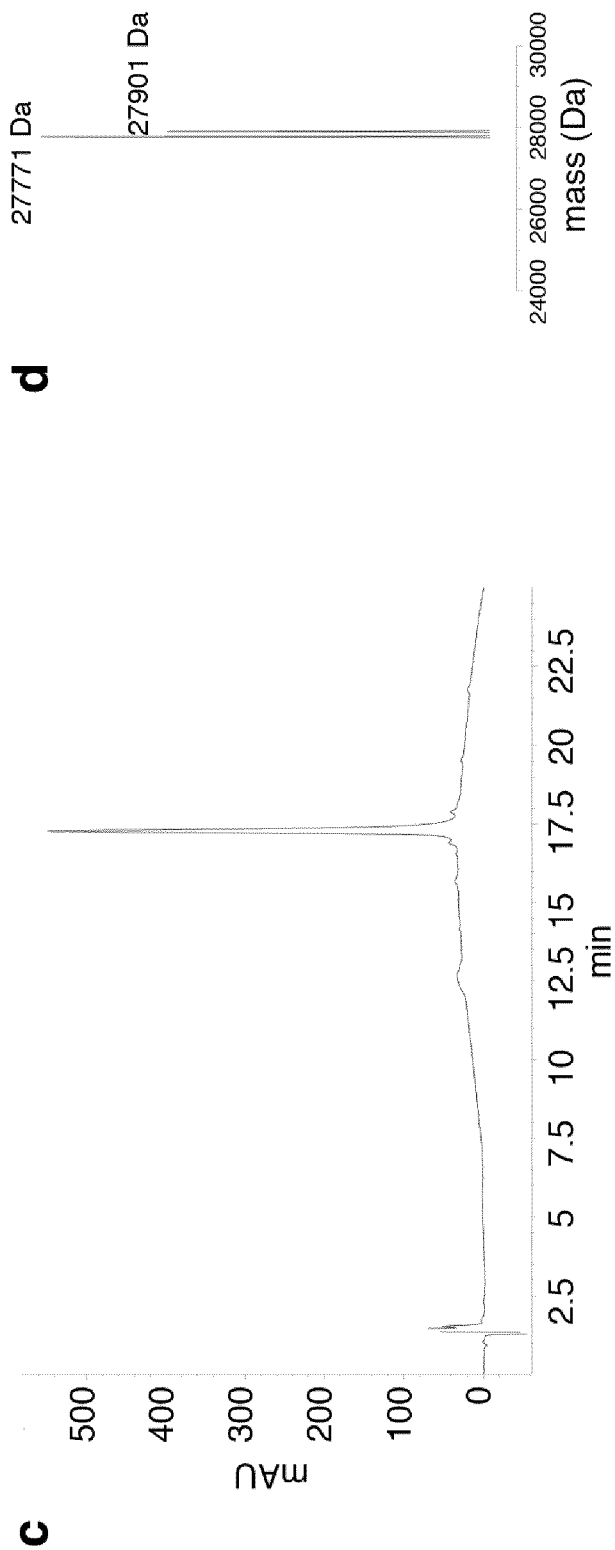

FIG. 2: Assembly and characterization of photoABPs and the biotin tagged photoABP-UbBpa31 probe. a) SDS-PAGE analysis of representative enzymatic conjugation of UbBpa31 to E2 (UBE2D3 C85K S22K double mutant) with ubiquitin E1 activating enzyme. Asterisk corresponds to a presumed diubiquitin species. b) Representative purification fractions of probe product after size-exclusion chromatography (SEC). c) RP-HPLC chromatogram for purified photoABP-UbBpa31. d) Deconvoluted mass spectrum for photoABP-UbBpa31. Observed mass=27901 Da, observed mass (-Met)=27771 Da. Expected mass=27908.87 Da, expected mass (-Met)=2777.67 Da.

Figure 3:
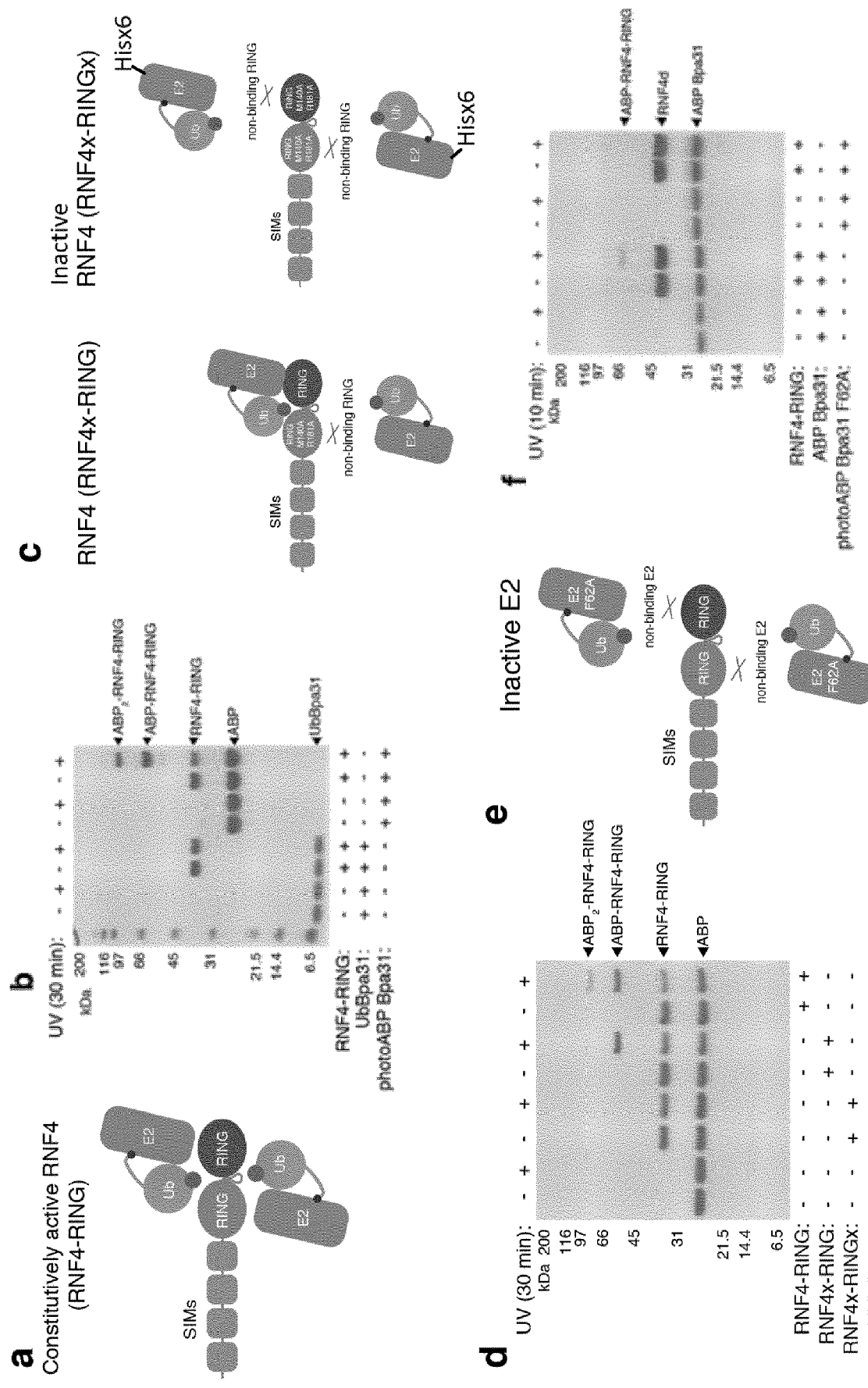
Figure 3:
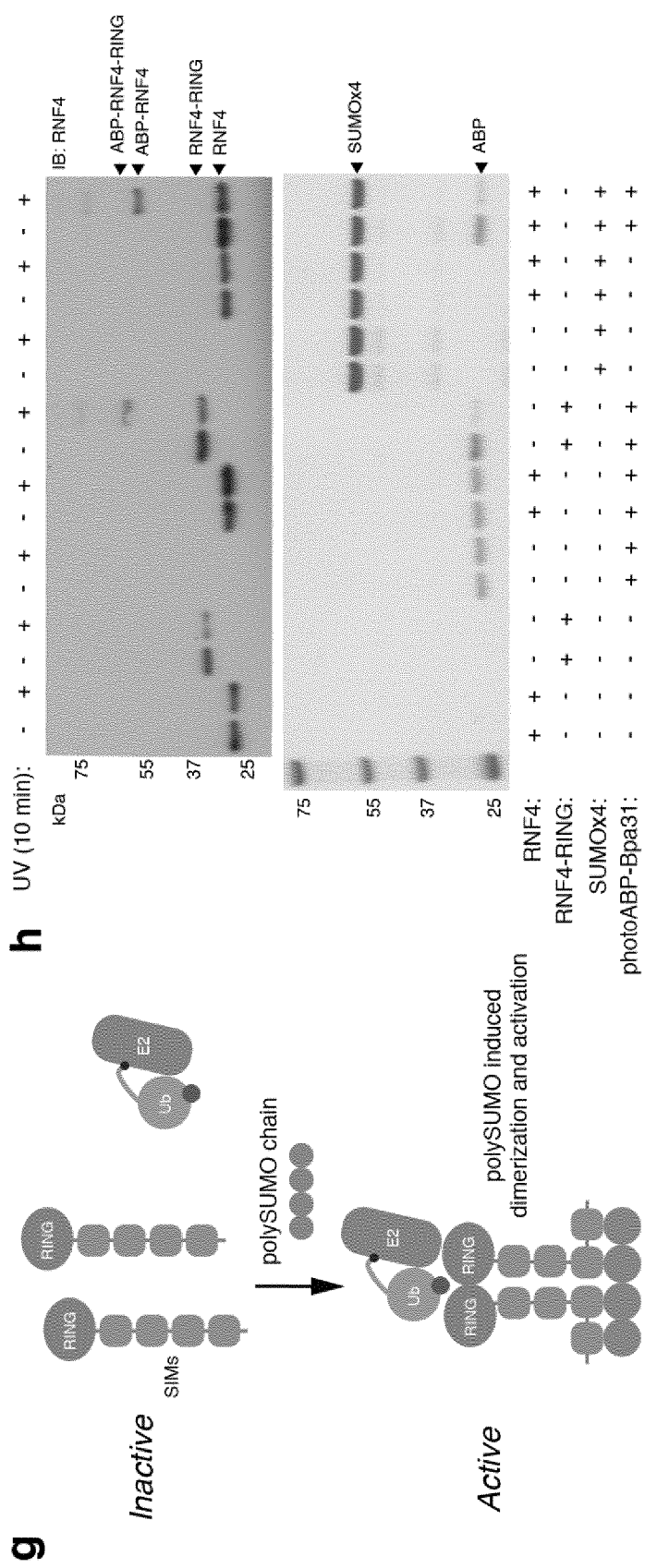

FIG. 3: Activity-dependent profiling of RNF4 E3 ligase activity. a) Constitutively active RNF-RING fusion protein can productively engage two E2~Ub conjugates. b) Probe photoABP-UbBpa31 (40 µM) undergoes two crosslinking reactions with RNF4-RING (10 µM). c) Engagement of one or both E2~Ub conjugates can be disrupted with a M140A R181A double mutation introduced into one or both RING domains in RNF-RING. d) Probe photoABP-UbBpa31 (40 µM) crosslinking is attenuated or abolished depending on whether one or both RING domains are mutated. e) Introduction of a F62A mutation into the E2 component should abolish E3 binding. f) Crosslinking is abolished with the photoABP-UbBpa31 F62A (probe concentration 5 µM). g) At concentrations below the $K_d$ for dimerization, RNF4 is inactive. Binding of poly-SUMO chains induces dimerization and E3 ligase activity. h) photoABP-UbBpa31 (5 µM) undergoes poly-SUMO chain (10 µM) dependent crosslinking of native RNF4 (100 nM) whereas RINF4-RING (50 nM) crosslinks independent of poly-SUMO chains.

Figure 4:
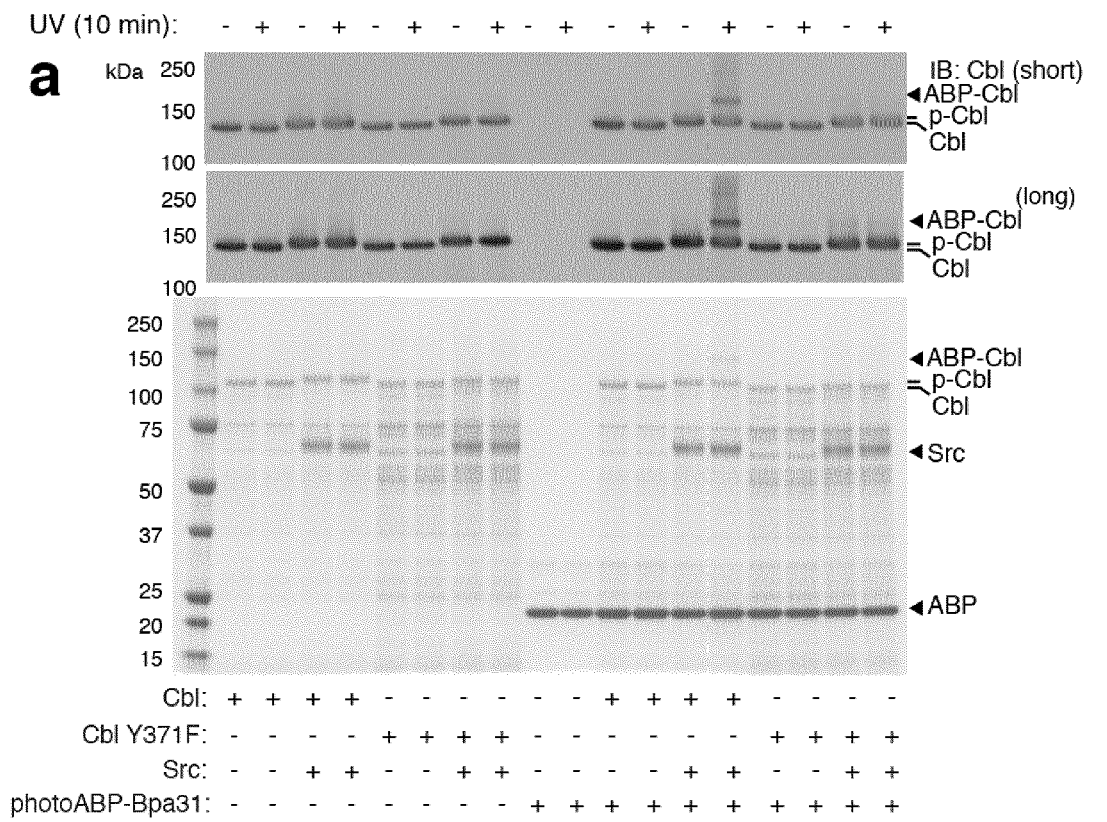
Figure 4:
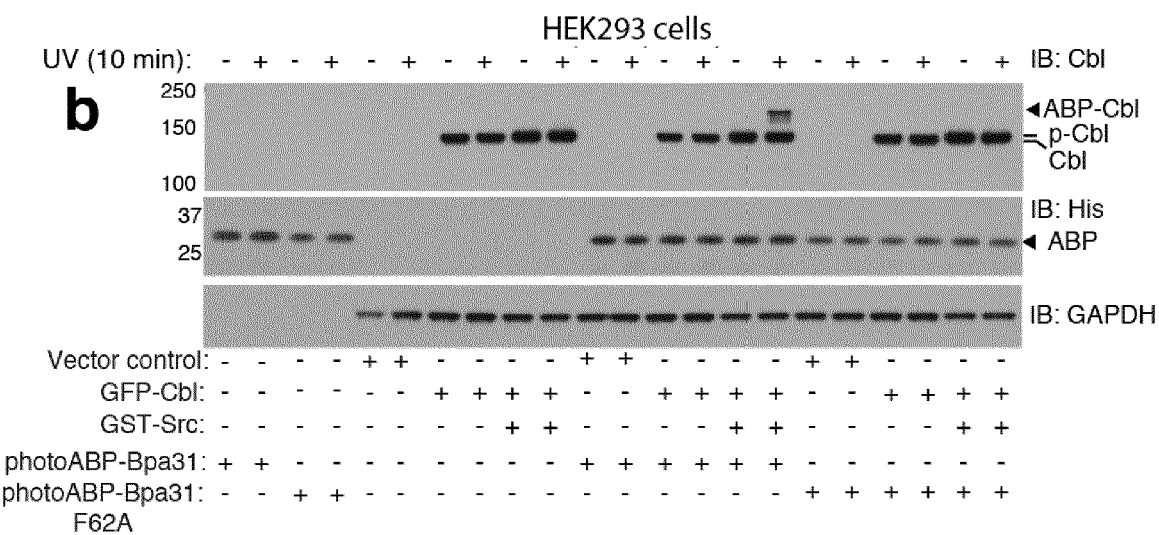
Figure 4:
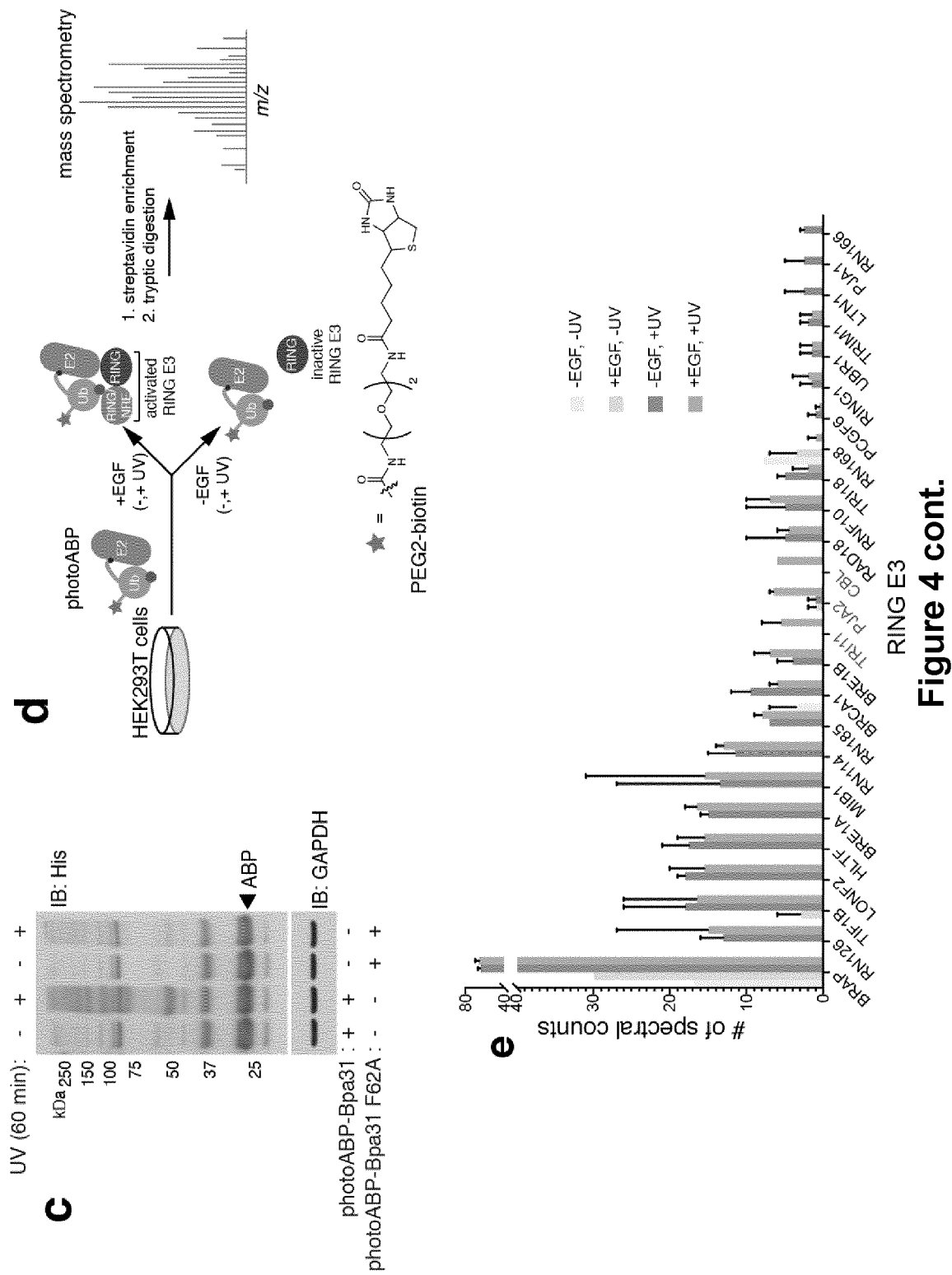

FIG. 4: Activity-dependent profiling c-Cbl E3 ligase activity and activity-based proteomic analyses of EGF-stimulated versus unstimulated HEK293T cells. a) Only c-Cbl (3 µM) preincubated with c-Src (1.5 µM) undergoes photoABP Bpa31 (5 µM) crosslinking. Crosslinking is not observed when Cbl Y371 (3 µM) (which cannot be phosphorylated at the activation site) is incubated with Src. Phosphorylation of Cbl results in reduced electrophoretic mobility. b) Transient overexpression of GFP-Cbl and c-Src in mammalian HEK293 cells. Extracts were treated with photoABP31 Bpa31 or the F62A control probe (5 µM). IB denotes immunoblot and the primary antibody used for detection is adjacent (i.e. anti-Cbl). c) Immunoblot analysis of HEK293T extracts with either photoABP-UbBpa31 or the photoABP-Bpa31 F62A control probe (10 µM). Blotting was carried out against the hexahistidine reporter tag present within the ABPs. Samples were irradiated for 60 minutes or irradiation was withheld. d) Schematic depicting activity-based proteomic workflow with biotinylated photoABP-Bpa31. e) Spectral counts obtained from ABP-profiled HEK293T cells. Search results were filtered against the PFAM domain term "RING" and only RING E3s with >2 spectral counts in any replicate experiment were plotted. Cells were serum-starved and either treated with or without EGF and with or without UV irradiation. Errors bar correspond to the standard error from two technical replicate LC-MS/MS analyses.

Figure 5:
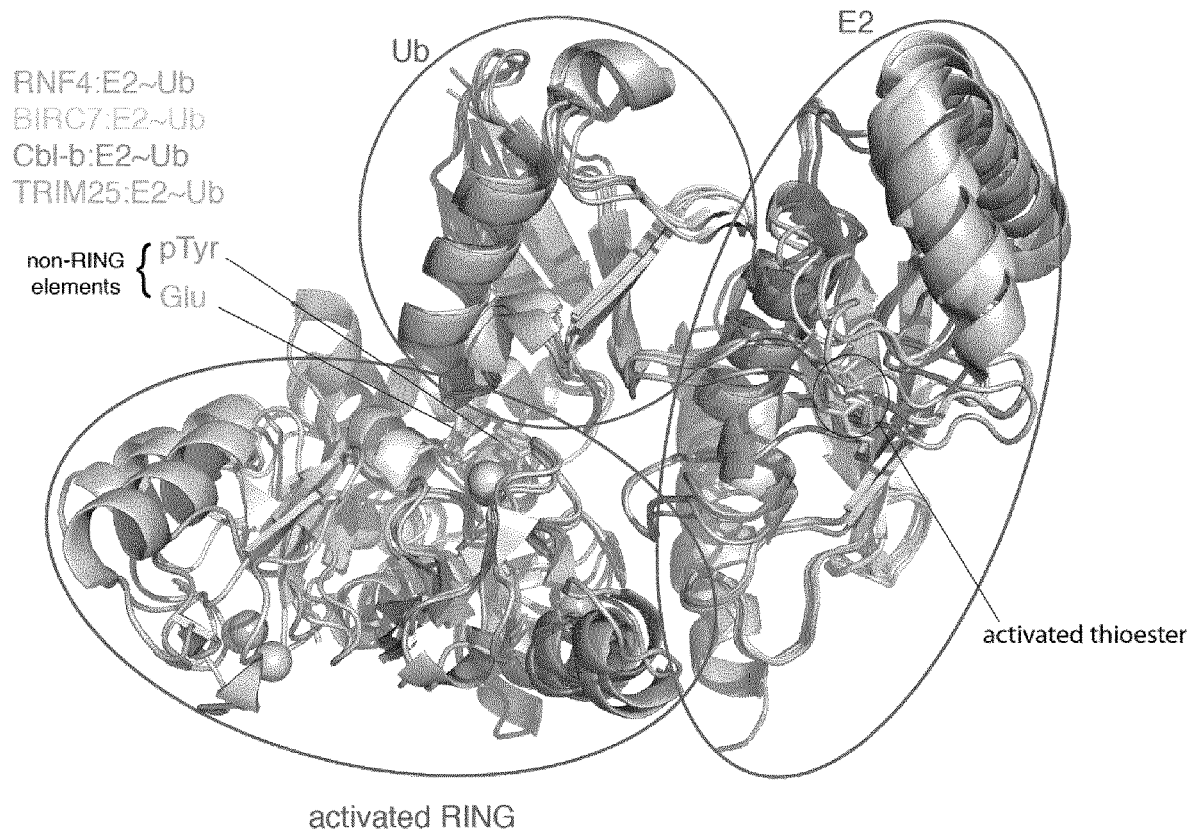

FIG. 5: Structural superposition of activated RING: E2~Ub complexes. Activated RING E3s bind E2~Ub and induce a "closed" E2~Ub conformation which activates the thioester for aminolysis (NB, in the presented crystal structures the the labile thioester has been relaced with an ester or isopeptide linkage by mutation of the E2 catalytic cysteine to serine or lysine, respectively). The closed conformation is induced by binding of the RING to a composite E2~Ub interface. Of particular significance, the Ub component is held in the closed conformation by interactions with RING protomer 2 in the case of RNF4 and BIRC7. For Cbl-b, a phosphotyrosine moiety (pTyr) serves as a non-RING element and facilitates the closed conformation. In the case of TRIM25, dimerization and the presence of a non-RING glutamate (Glu) residue facilitates the closed conformation.

Figure 6:
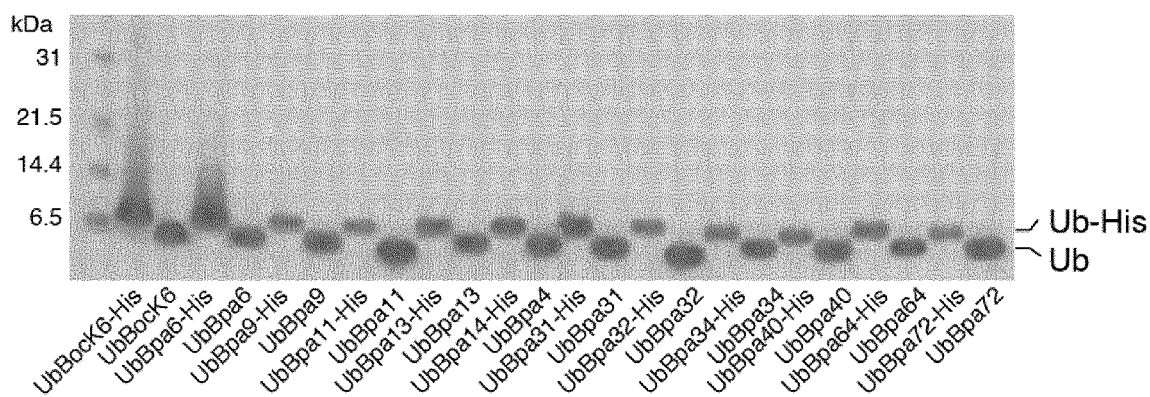

FIG. 6: Incorporation of the photocrosslinking amino acid p-benzoyl-L-phenylalanine (Bpa) into RING-proximal sites of ubiquitin. SDS-PAGE analysis and visualization by Coomasie staining. As a positive control, the reference amino acid t-butyloxycarbonyl-L-lysine (BocK) was incorporated into Ub at position 6. To facilitate purification a C-terminal His tag was appended to Ub which was subsequently removed by treatment with the deubiquitinating enzyme UCH-L3. For each mutant, samples pre- and post-UCH-L3 treatment were analysed FIG. 7: Electrospray ionization mass spectra for ubiquitin Bpa mutants. Spectra correspond to Ub after cleavage of the C-terminal His-tag. With the exception of the amber mutant clone for position 6, Ub is expressed with an N-terminal MGS motif. Introduction of the DNA coding sequence for this facilitated cloning. For these latter clones the N-terminal methionine is cleaved by cellular methionyl aminopeptidase to various degrees. A) UbBpa6, observed mass=8686 Da; expected=8787.95 Da. B) UbBpa9 (-Met), observed mass=8857 Da; expected=8859.15 Da. UbBpa9, observed mass=8988 Da; expected=8990.35 Da. C) UbBpa11 (-Met), observed mass=8830 Da; expected=8832.08 Da. UbBpa11, observed mass=8961 Da; expected=8963.28 Da. D) UbBpa13 (-Met), observed mass=8845 Da; expected=8847.1 Da. E) UbBpa14 (-Met), observed mass=8857 Da; expected=8859.15 Da. UbBpa14, observed mass=8988 Da; expected=8990.35 Da. F) UbBpa31 (-Met), observed mass=8830 Da; expected=8832.12 Da. UbBpa31, observed mass=8961 Da; expected=8963.32 Da. G) UbBpa32 (-Met), observed mass=8845 Da; expected=8845.17 Da. UbBpa32, observed mass=8976 Da; expected=8976.37 Da. H) UbBpa34 (-Met), observed mass=8830 Da; expected=8831.14 Da. UbBpa34, observed mass=8961 Da; expected=8962.34 Da. I) UbBpa40 (-Met), observed mass=8831 Da; expected=8832.12 Da. UbBpa40, observed mass=8962 Da; expected=8963.32 Da. J) UbBpa64 (-Met), observed mass=8830 Da; expected=8831.14 Da. UbBpa64, observed mass=8961 Da; expected=8962.34 Da. K) UbBpa72 (-Met), observed mass=8803 Da; expected=8804.07 Da. Observed peak at 8836 Da corresponds to an unidentified adduct.

Figure 8:
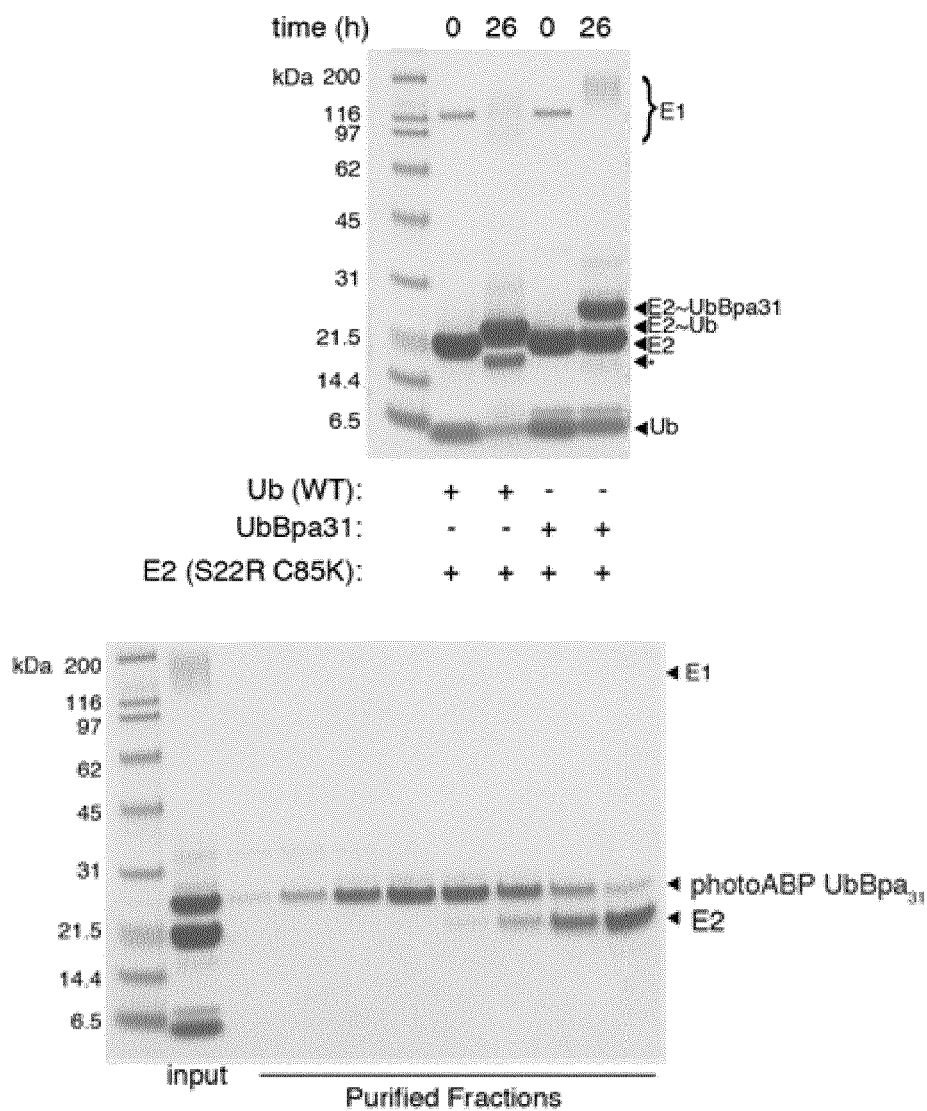

FIG. 8: Representative enzymatic conjugation of UbBpa31 to E2 via a stabilized isopeptide linkage to furnish photoABP-UbBpa31. SDS-PAGE analysis and visualization by Coomasie staining (top). Probe product was purified by size exclusion chromatography (bottom).

Figure 9:
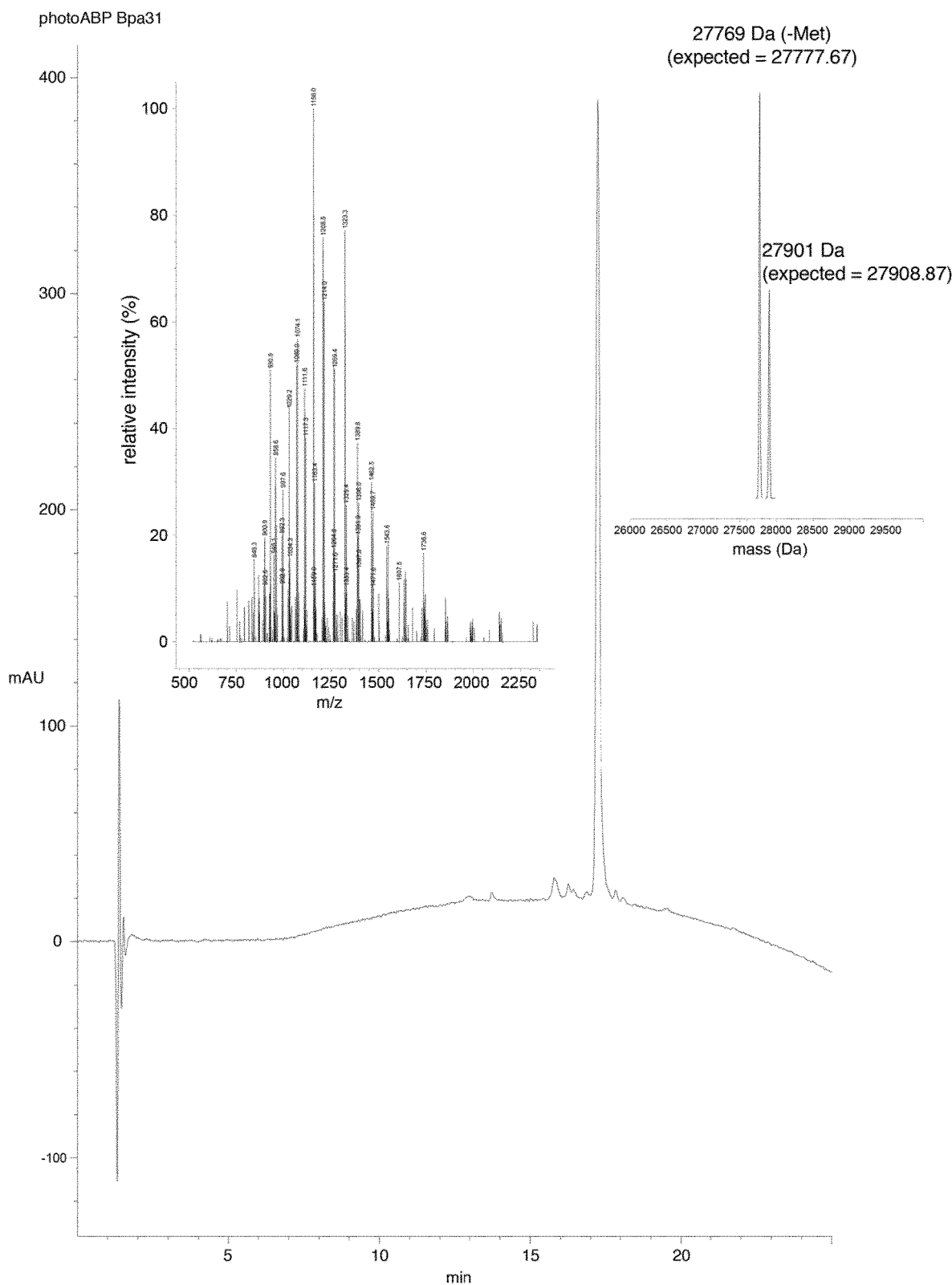

FIG. 9: Representative LC-MS analysis for photoABP-Bpa31. HPLC chromatogram measured at 214 nm. PhotoABP Bpa31 (-Met), observed mass=27769 Da; expected mass=27777.67 Da. PhotoABP Bpa31 (-Met), observed mass=27901 Da; expected mass=27908.87 Da.

Figure 10:
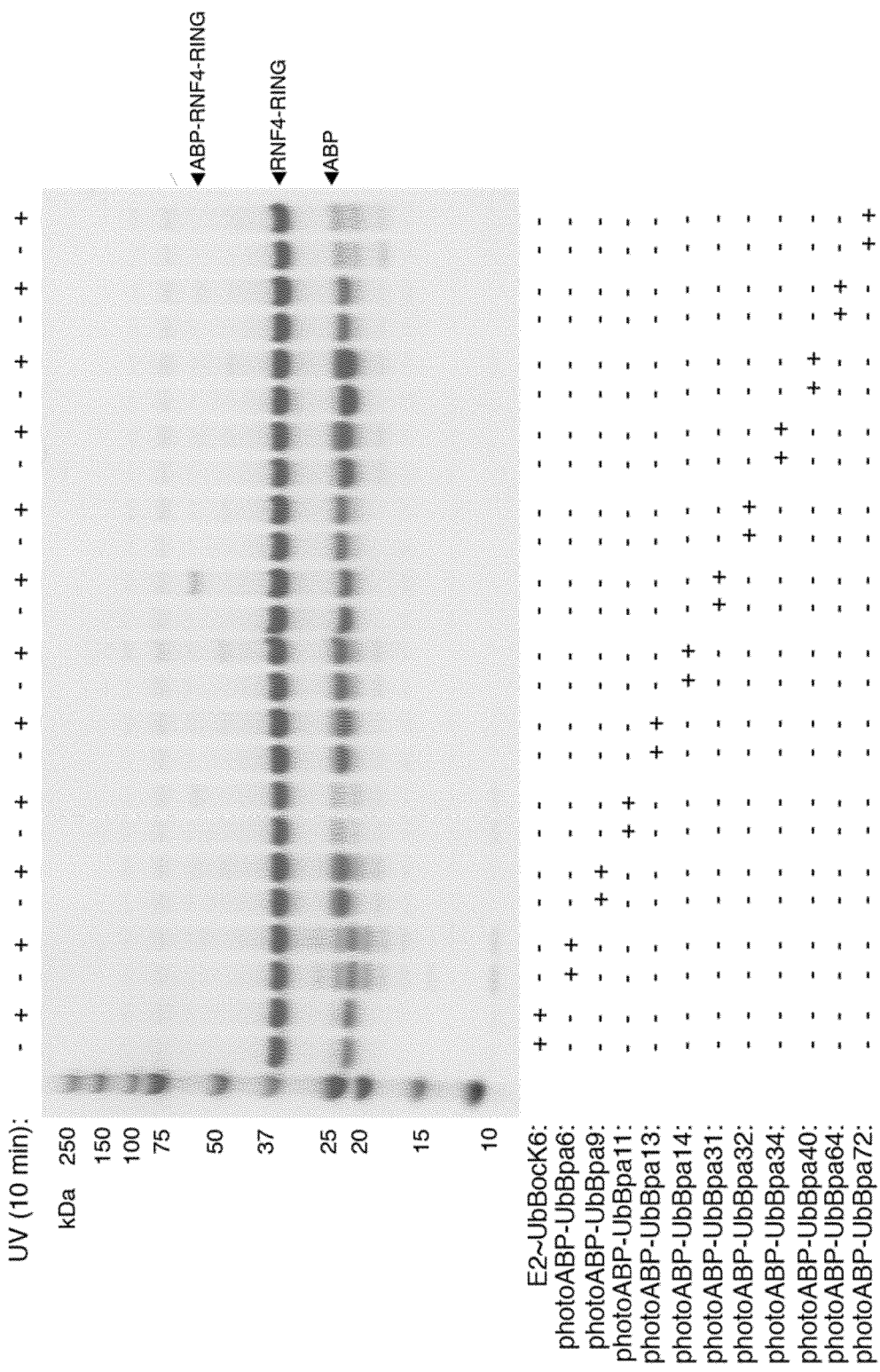

FIG. 10: Assessment of RNF4-RING photocrosslinking efficiency for incorporation of Bpa at 10 different Ub positions within isopeptide-linked E2~Ub conjugate. Significant incorporation was only achieved with incorporation of Bpa at position 31, furnishing probe photoABP-UbBpa31. The reference amino acid t-butyloxycarbonyl-L-lysine (BocK) and Bpa were incorporated at position 6 as this site is highly permissive to unnatural amino acid incorporation and served as controls.

Figure 11:
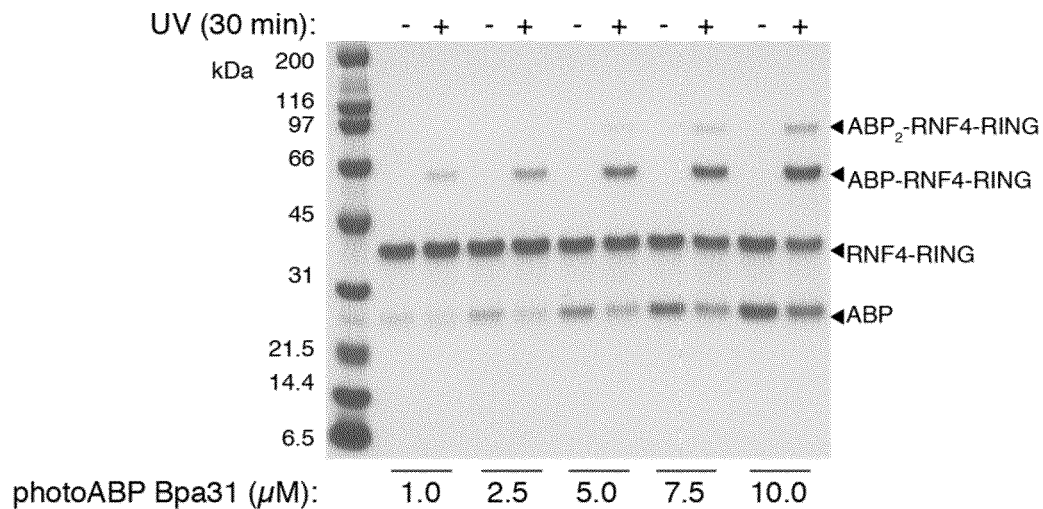

FIG. 11: Dose responsive photocrosslinking of RNF4-RING. Photocrosslinking efficiency of RNF4-RING was responsive to increasing concentrations of photoABP-UbBpa31.

Figure 12:
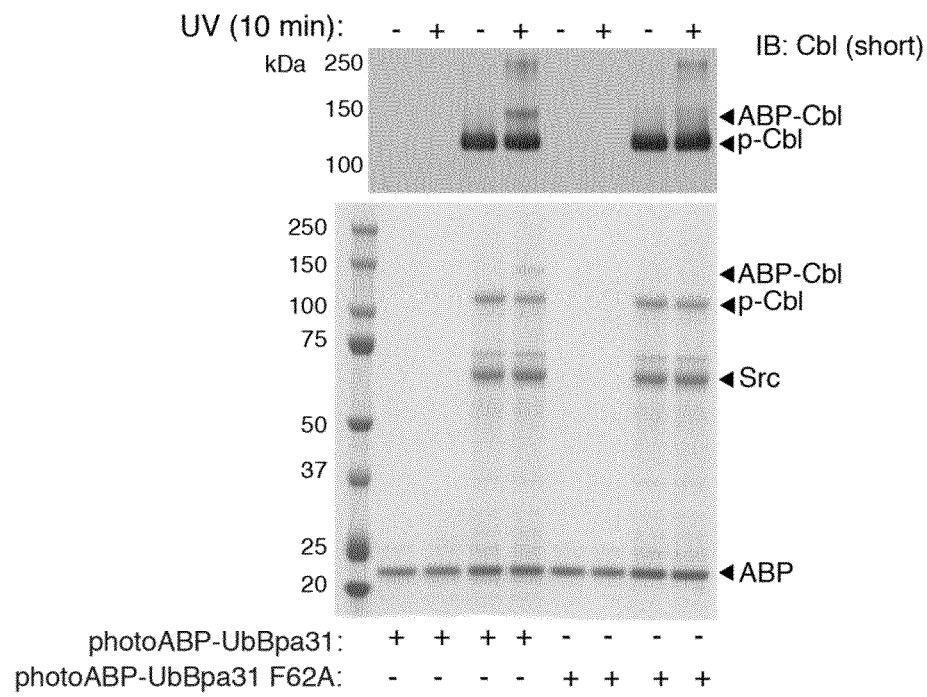

FIG. 12: Photocrosslinking of phosphorylated c-Cbl with photoABP-UbBpa31 and the photoABP-UbBpa31 F62A control probe. Purified c-Cbl (3 µM) was preincubated with c-Src (1.5 µM) in the presence of ATP (5 mM) for 45 min at 37° C. Reaction mixture was then profiled with the specified probes (5 µM). The probe photoABP-Bpa31 undergoes c-Cbl crosslinking whereas photoABP-Bpa31F62A does not.

Figure 13:
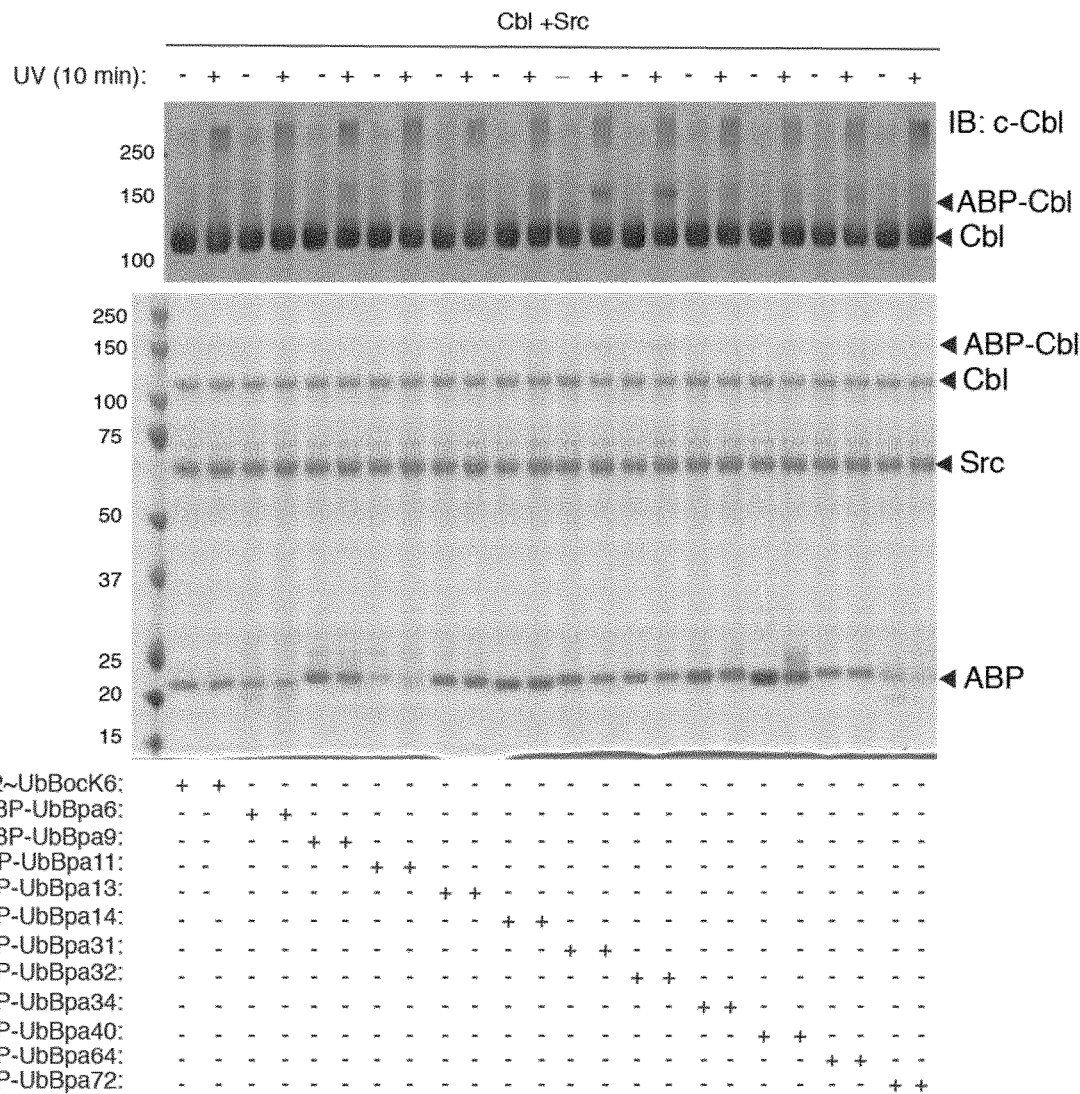

FIG. 13: Comparison of photocrosslinking efficiency for Bpa incorporation at multiple positions within ubiquitin. c-Cbl (3 µM) was phosphorylated by incubation with c-Src (1.5 3 µM) prior to probe analysis. Only incorporation of Bpa at positions 31 and 32 furnishes a functional probe.

Figure 14:
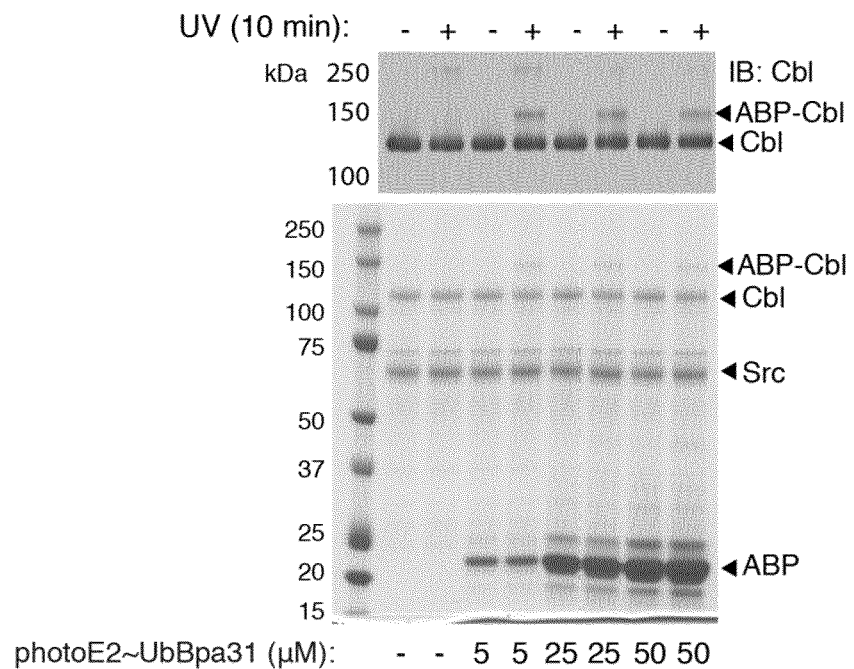

FIG. 14: Dose-response analysis of Cbl crosslinking. C-Cbl (3 µM) was phosphorylated by incubation with c-Src (1.5 µM) prior to probe analysis. No increase in Cbl labelling efficiency was observed as a result of increasing photoABP-UbBpa31 concentration beyond 5 µM.

Figure 15:
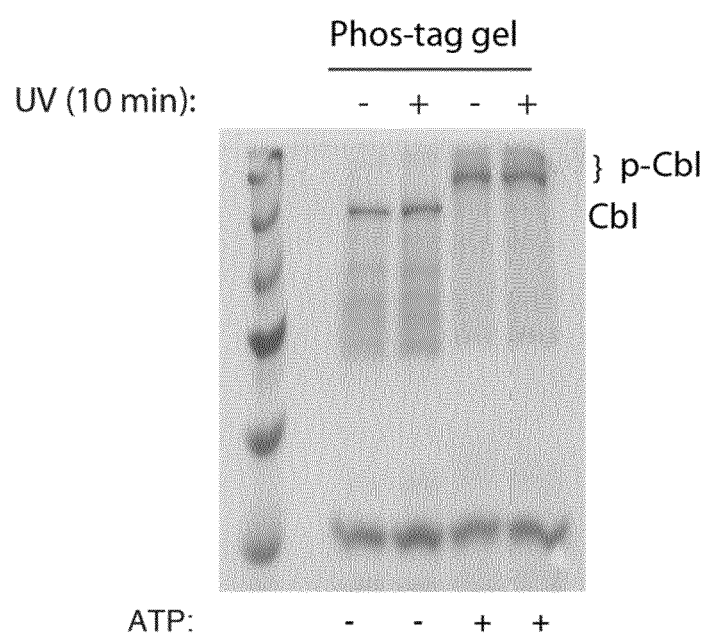

FIG. 15: Phostag SDS-PAGE analysis of c-Src treated c-Cbl. Reduced electrophoretic mobility of c-Cbl is only observed in the presence of ATP. As the gel shift is quantitative, this indicates that phosphorylation must too be quantitative. However, crosslinking efficiency with photoABP-UbBpa31 was not dose responsive beyond 5 µM. This is consistent with c-Cbl becoming phosphorylated at multiple sites but substoichiometrically at Y371.

Figure 16:
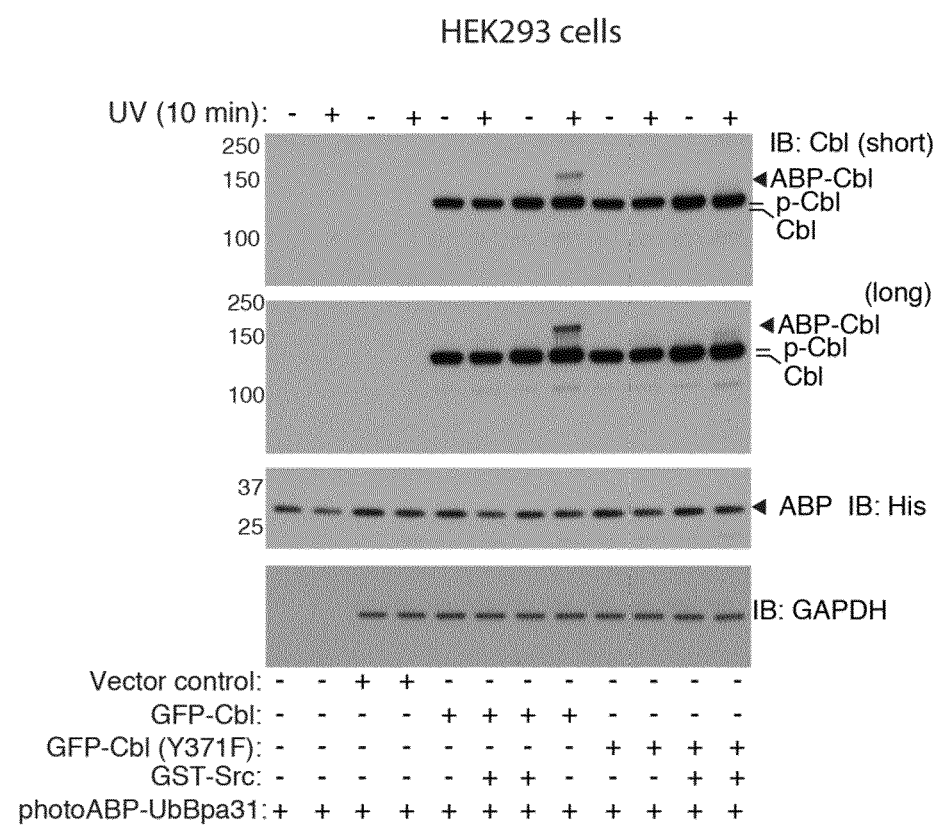

FIG. 16: Photocrosslinking of cellular Cbl remains strictly dependent on the presence of Y371. C-Cbl (3 µM) was phosphorylated by incubation with c-Src (1.5 µM) prior to probe analysis. No increase in Cbl labelling efficiency was observed as a result of increasing photoABP-UbBpa31 concentration beyond 5 µM. This is may be due to substoichiometric phosphorylation at Y371.

Figure 17:
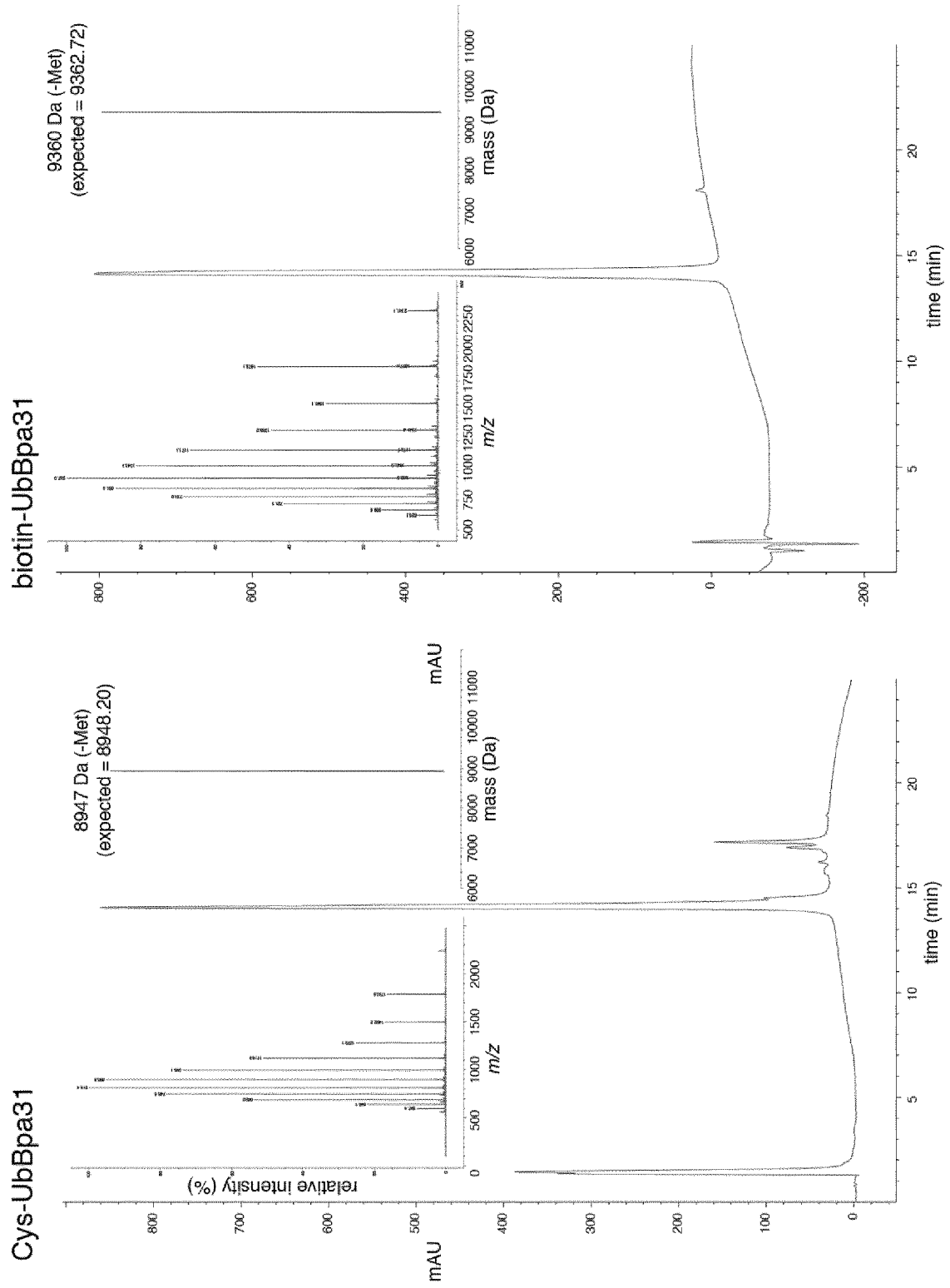
Figure 17:
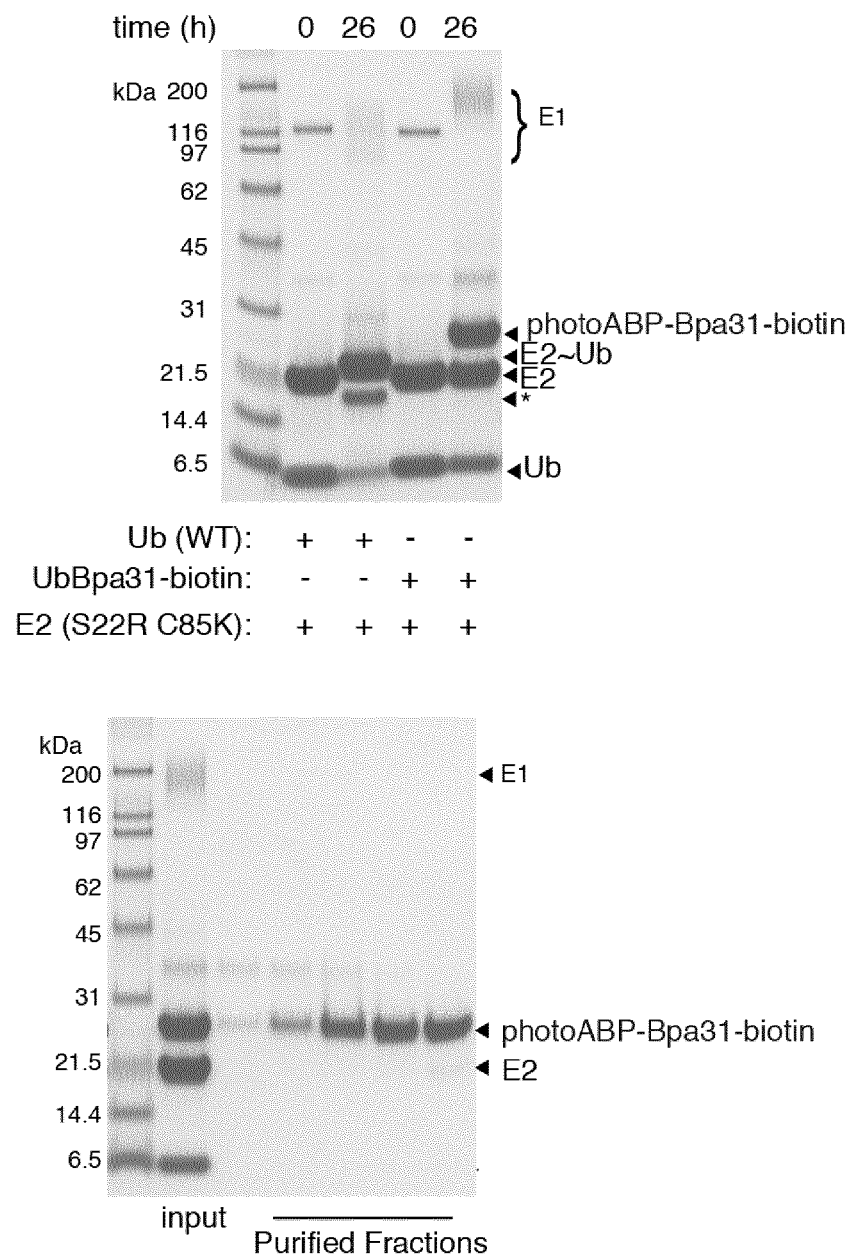

FIG. 17: Biotin labelling of Cys-tagged UbBpa31 and enzymatic conjugation to E2. LC-MS characterization of UbBpa31 expressed with an N-terminal MGCSSG labelling motif (observed mass=8947 Da; expected mass=8948.2 Da) (top left). Cysteine labelling motif was alkylated with EZ-Link Iodoacetyl-PEG2-Biotin (Thermofisher). Product was purified by preparative RP-HPLC and characterized by LC-MS (observed mass=9360 Da; expected mass=9362.72 Da) (top right). Refolded biotin-tagged UbBpa31 was enzymatically conjugated onto E2 and the probe was purified by size-exclusion chromatography (bottom).

Figure 18:
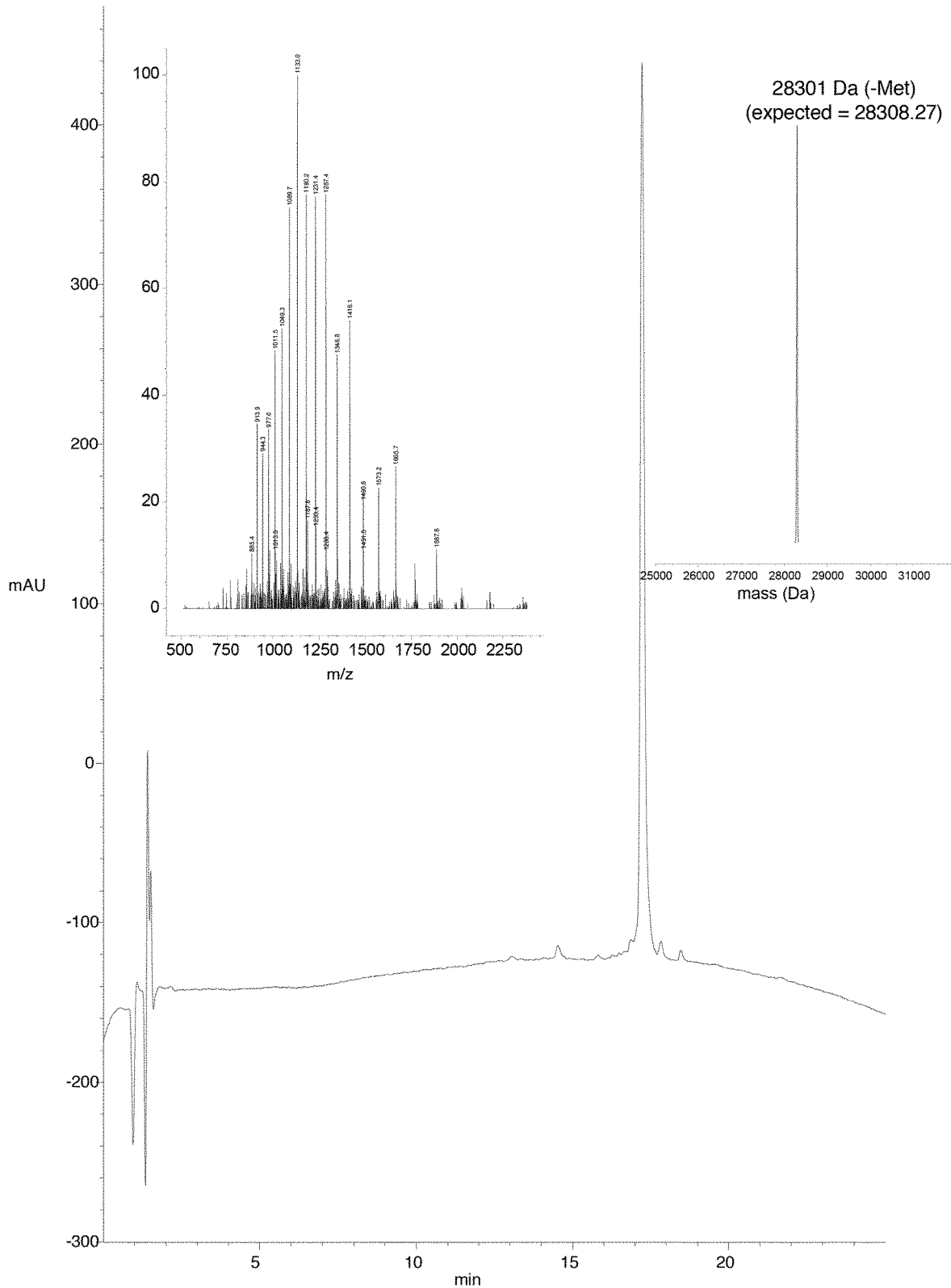

FIG. 18: LC-MS analysis for biotin-photoABP-Bpa31. HPLC chromatogram measured at 214 nm. photoABP Bpa31 (-Met), observed mass=28301 Da; expected mass=28308.27 Da.

Figure 19:
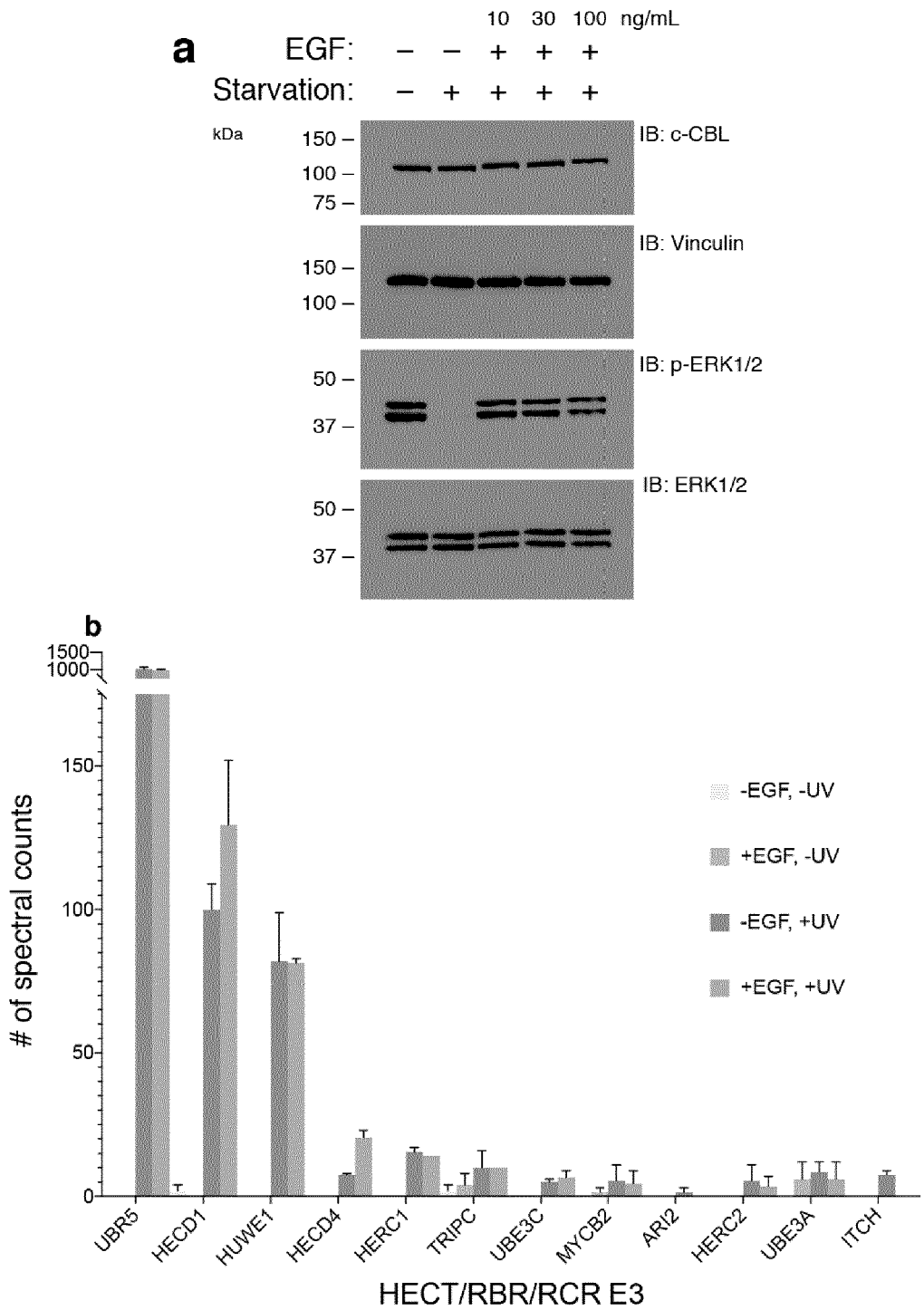
Figure 19:
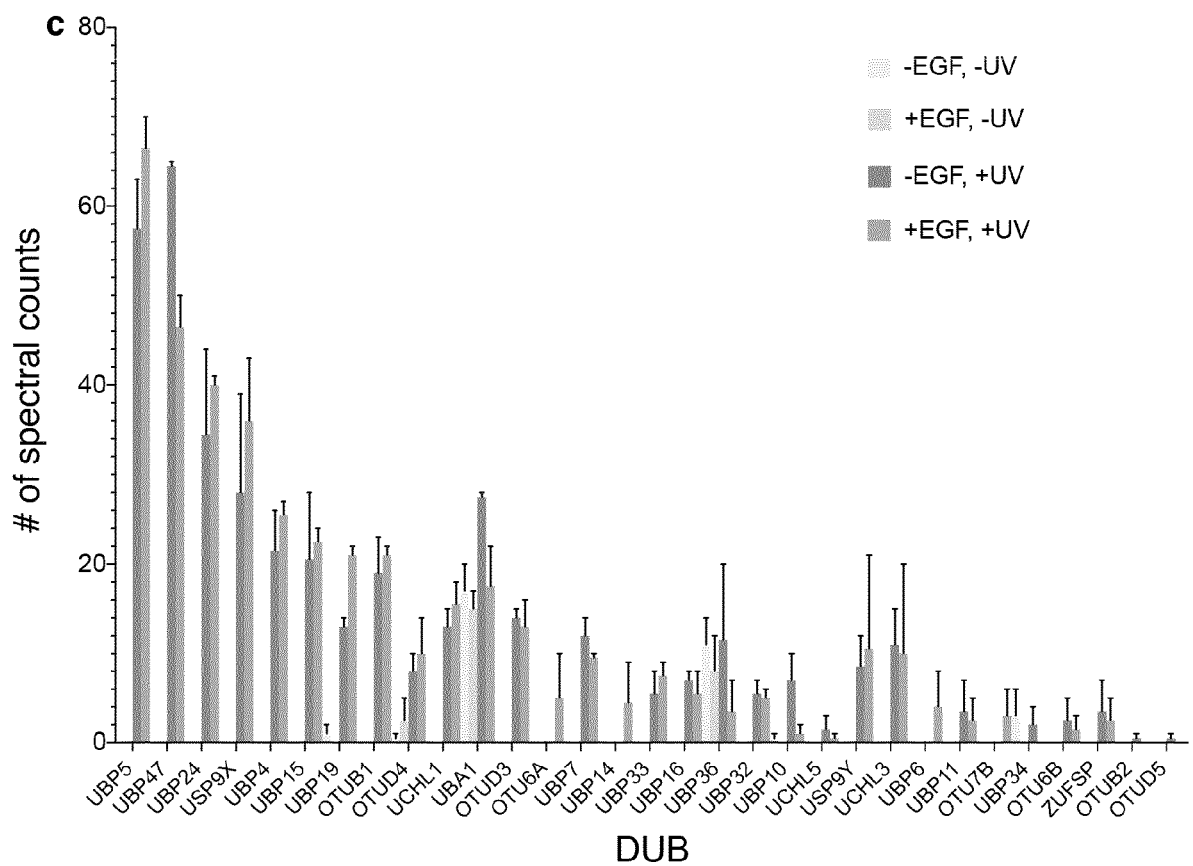

FIG. 19: Confirmation of receptor tyrosine kinase activation and assessment of non-RING E3 photocrosslinking. a) EGF-dependent receptor activation is confirmed by immunoblotting for ERK1/2 phosphorylation. HEK293T cells were serum-starved and stimulated with recombinant EGF. Cells were treated with the proteasome inhibitor MG132 prior to stimulation. N.B. for proteomic experiment, cells were treated with MG132 and bafilomycin. b) Detection of other ubiquitin system components by activity-based proteomics with biotinylated photoABP-UbBpa31. Spectral counts obtained from ABP-profiled HEK293T cells. Search results were filtered against the PFAM domain term "HECT, IBR and zf-UBR" and only RING E3s with >2 spectral counts in any replicate experiment were plotted. Cells were serum-starved and either treated with or without EGF and with or without UV irradiation. Errors bar correspond to the standard error from two technical replicates. c) As above but DUBs were filtered using a combination of PFAM domain terms and manual curation.

Figure 20:
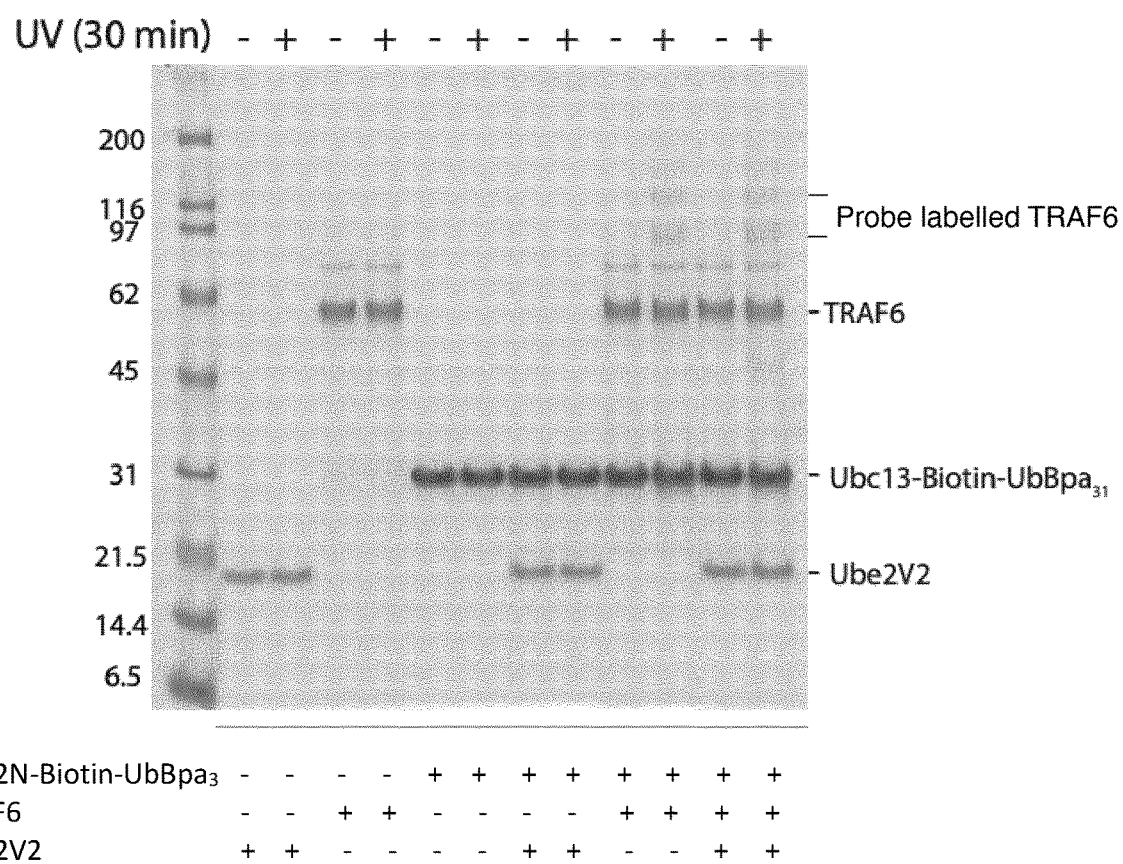

FIG. 20: Confirmation that the UBE2N/Ubc13 photo-crosslinking activity-based probe undergoes covalent labelling of its cognate E3 TRAF6 in a UV-dependent manner. Experiments were also carried out in the presence of a UBE2N substrate receptor (Ube2V2). Its presence did not appear to influence activity towards TRAF6.

DETAILED DESCRIPTION OF THE INVENTION

ABPs based on an engineered E2~Ub conjugate where the labile cysteine thioester has been replaced with a more stable linkage chemistry, such as a lysine isopeptide (Plechanovova, A. et al., 2012, supra), are disclosed herein.

The activated ubiquitin molecules of the invention are surprisingly effective as ABPs when conjugated to an E2 conjugating enzyme. The ABPs of the invention are effective in activity profiling RING E3 enzymes, RING E1 enzymes and/or deubiquitinating enzymes in diverse sample types. The activated ubiquitin molecules, conjugates, uses and methods of the invention are now described in detail.

In the discussion that follows, reference is made to a number of terms, which have the meanings provided below, unless a context indicates to the contrary. The nomenclature used herein for defining compounds, in particular the molecules according to the invention, is in general based on the rules of the IUPAC for chemical compounds, specifically the "IUPAC Compendium of Chemical Terminology (Gold Book)".

The term "comprising" or variants thereof will be understood to imply the inclusion of a stated element, integer or step, or group of elements, integers or steps, but not the exclusion of any other element, integer or step, or group of elements, integers or steps.

The term "consisting" or variants thereof will be understood to imply the inclusion of a stated element, integer or step, or group of elements, integers or steps, and the exclusion of any other element, integer or step or group of elements, integers or steps.

The term "aryl" is well known in the art and defines all univalent groups formed by removing a hydrogen atom from an arene ring carbon. The term "arene" defines monocyclic and polycyclic aromatic hydrocarbons.

The term "heteroaryl" defines an aryl in which one or more methine (—C=) and/or vinylene (—CH=CH—) groups have been replaced by trivalent or divalent heteroatoms respectively, in such a way as to maintain the continuous π-electron system characteristic of aromatic systems.

The term "alkyl" is well known in the art and defines univalent groups derived from alkanes by removal of a hydrogen atom from any carbon atom, wherein the term "alkane" is intended to define cyclic or acyclic branched or unbranched hydrocarbons having the general formula $CnH_{2n+2}$, wherein n is an integer $\geq 1$.

The term "hydrocarbyl" is well known in the art and defines all univalent groups formed by removing a hydrogen atom from a hydrocarbon. The term "hydrocarbon" is equally well known and means herein all aliphatic and aromatic compounds consisting of carbon and hydrogen only, including branched, unbranched, acyclic and cyclic alkanes, alkenes and alkynes. For the avoidance of doubt, cycloalkanes and cycloalkenes lie within the scope of this definition of hydrocarbon.

The term "halo" is well known in the art and defines a halogen radical that, when bonded to a carbon radical makes a fluoride, chloride, bromide or iodide compound.

The activated ubiquitin molecule of the invention comprises a photocrosslinker moiety in place of a glutamine residue at position 31 and/or an aspartic acid residue at position 32 of ubiquitin. Ubiquitin consists of 76 amino acids with the following sequence (SEQ ID:1):

MQIFVKTLTGKTITLEVEPSDTIENVKAKIQDKEGIPPDQQRLIFAGKQ
LEDGRTLSDYNIQKESTLHLVLRLRGG

Replacing the glutamine residue at position 31 and/or the aspartic acid residue at position 32 (underlined and emboldened in the above sequence) with a photocrosslinker moiety results in surprisingly effective photocrosslinking between the activated ubiquitin molecule and an E2 conjugating enzyme (see below).

In some embodiments, the photocrosslinker moiety is in place of the glutamine residue at position 31 or the aspartic acid residue at position 32 of ubiquitin. In one embodiment, the photocrosslinker moiety is in place of the glutamine residue at position 31 of ubiquitin.

The photocrosslinker moiety may be any moiety that is capable of replacing the glutamine residue at position 31 and/or the aspartic acid residue at position 32 of ubiquitin and, on irradiation with photons, forming a linker between the ubiquitin molecule and an E2 conjugating enzyme. Preferably, the activated ubiquitin molecule is stable in the absence of photons, allowing it to be stored in suitable conditions before use. In some embodiments, the activated ubiquitin molecule is stable in the presence of natural light and in further embodiments is stable in the presence of natural and indoor artificial lighting used to increase visibility (i.e. typical domestic lighting comprised mainly of visible light).

"Stable" is used herein to mean that the amount of chemical decomposition of the material or substance that occurs over time is not so severe to render the material or substance incapable of practical use. This allows for some degree of chemical decomposition of the material or substance, ranging from negligible chemical decomposition to levels of chemical decomposition wherein the amount of material or substance that has not decomposed is capable of practical use.

The skilled person is able to assess which conditions are suitable for storage of the activated ubiquitin molecule. For example, where the activated ubiquitin molecule is stable in the absence of photons but not in the presence of natural light, the skilled person is aware that the molecule should be stored in the dark; and where the activated ubiquitin molecule is unstable at room temperatures, the molecule should be stored in a refrigerator.

In certain embodiments, the photocrosslinker moiety is an unnatural amino acid, i.e. a modified natural amino acid which may be entirely or partly synthetic. Typically, the unnatural amino acid is derived from modification of a natural amino acid with a functional group that is capable of forming a linker between the ubiquitin molecule and an E2 conjugating enzyme on irradiation with photons.

In some embodiments, the unnatural amino acid comprises any one or a combination selected from the group consisting of diarylketones, diazirines, arylazides, diaryl/heteroarylketones, diheteroarylketones, heteroarylazides and 2-aryl-5-carboxytetrazoles. In certain embodiments, the unnatural amino acid comprises one type of functional group selected from the group consisting of diarylketones, diazirines, arylazides, diaryl/heteroarylketones, diheteroarylketones, heteroarylazides and 2-aryl-5-carboxytetrazoles. When the unnatural amino acid comprises diarylketones, arylazides and 2-aryl-5-carboxytetrazoles, the aryl is optionally substituted and may be selected from the group consisting of phenyl or naphthalenyl. When the unnatural amino acid comprises diaryl/heteroarylketones, diheteroarylketones and heteroarylazides, the heteroaryl is optionally substituted and may be selected from the group consisting of indolyl, imidazolyl, pyridyl, thiophenyl and furanyl.

The aryl or heteroaryl may be substituted at one or more carbon atoms with any one or a combination selected from the group consisting of $C_{1-4}$hydrocarbyls, $C_{1-4}$alkyloxy, $C_{1-4}$haloalkyls, hydroxy and halo. In some embodiments, halo is fluoro. In certain embodiments, the aryl or heteroaryl is optionally substituted with any one or a combination selected from the group consisting of methyl, ethyl, propyl, butyl, methoxy, ethoxy, propoxy, butoxy, trifluoromethyl, hydroxy and fluoro.

In some embodiments, the unnatural amino acid comprises any one or a combination of the functional groups selected from the group consisting of diarylketones, diazirines and arylazides (Pham N. D., Parker R. B., Kohler J. J., Curr. Opin. Chem. Biol., (2013), 17, 1, 90-101; Kauer, J. C., Erickson-Viitanen S., Wolfe H. R., DeGrado W. F., J. Biol. Chem., (1986), 261, 23, 10695-10700).

In specific embodiments, the unnatural amino acid comprises a diarylketone. Often, the diarylketone is any one selected from the group consisting of benzophenone, methylbenzophenone, dimethylbenzophenone, methoxybenzophenone, dimethoxybenzophenone, tertbutoxybenzophenone, ditertbutoxybenzophenone, trifluoromethylbenzophenone, di(trifluoromethyl)benzophenone, tetrakis(trifluoromethyl)benzophenone, hydroxybenzophenone, dihydroxybenzophenone, trihydroxybenzophenone, fluorobenzophenone, difluorobenzophenone and trifluorobenzophenone.

In certain embodiments, the unnatural amino acid comprises benzophenone. Often, the unnatural amino acid is derived from any one of the group consisting of phenylalanine, tryptophan and histidine. In specific embodiments, the unnatural amino acid is derived from phenylalanine.

In specific embodiments, the photocrosslinker moiety is p-benzoyl-L-phenylalanine.

The activated ubiquitin molecule of the invention may be derived from ubiquitin from any eukaryotic organism. Typically, however, the ubiquitin of the invention is derived from an animal, for example a mammal. In some embodiments, the activated ubiquitin molecule of the invention is derived from a human.

The activated ubiquitin molecule of the invention may comprise a reporter tag. The purpose of the reporter tag is to allow analytical detection of the activated ubiquitin. Thus, any tag suitable for binding to ubiquitin for detection, for example by fluorescence, may be employed.

In some embodiments, the reporter tag comprises any one, or a combination selected from the group consisting of biotin, epitopes and fluorophores. Epitopes are recognized by common antibodies which bind to specific epitopes. When the reporter tag comprises an epitope, it is able to bind to an antibody and allow for localization, purification and molecular characterization of the activated ubiquitin molecule. Epitopes include Myc-tag, HA-tag, FLAG-tag, GST-tag, 6×His, V5-tag and OLLAS.

Fluorophores are fluorescent tags. When the reporter tag comprises a fluorophore the activated ubiquitin molecules of the invention may be detected by fluorescent microscopy or by the naked eye. Fluorophores include fluorescein; green fluorescent proteins, for example the optimized S65T mutant, enhanced green fluorescent protein (EGFP), the monomeric A206K mutant, superfolder GFP (sfGFP), Emerald, TagBFP, mCerulean3, mCitrine/mVenus, tdTomato, mCherry, mApple, mKate2 and mNeptune; FLAsH-EDT2 and ReAsH-EDT2.

When the reporter tag comprises biotin, it is able to bind to its natural ligand, i.e. avidin, streptavidin or neutravidin to allow for localization, purification and molecular characterization of the activated ubiquitin molecule. The natural ligands may themselves be bound to fluorescent probes comprising any of the fluorophores listed above; enzyme reporters such as horseradish peroxidase or alkaline phosphatase; or anti-biotin antibodies.

Detection of the activated ubiquitin molecules comprising reporter tags may be via fluorescent microscopy (or the naked eye), electron microscopy, enzyme-linked immunosorbent assays (ELISAs), and/or Western blots.

In certain embodiments, the reporter tag is a biotin moiety. This may be covalently linked to the ubiquitin or activated ubiquitin molecule of the invention. In some embodiments, the biotin moiety is covalently linked to the ubiquitin or activated ubiquitin molecule via a terminal cysteine-, serine-, threonine- or tyrosine-containing motif. The terminal motif may be C- or N-terminal but is typically N-terminal. In certain embodiments, the terminal motif is an N-terminal cysteine-containing motif. In more specific embodiments, the terminal motif has the sequence MGCSSG (SEQ ID: 2). Biotin and epitope tags allow enrichment of crosslinked, activated RING E3s enabling their identification, and activity quantification, by mass spectrometry.

The conjugate molecule of the second aspect of the invention comprises the activated molecule of the first aspect conjugated to an E2 conjugating enzyme. During ubiquitination, ubiquitin is transferred onto the catalytic cysteine in E2, forming a labile thioester-linked E2 intermediate (E2~Ub) before subsequent transfer of the ubiquitin to a lysine residue on the target protein.

To prevent dissociation of the activated ubiquitin molecule of the invention from the E2 conjugating enzyme, the catalytic cysteine residue of the E2 enzyme may be replaced with a residue that forms a more stable linker, such as a lysine residue. Therefore, in some embodiments, the E2 conjugating enzyme comprises a lysine residue in place of the catalytic cysteine residue. In certain embodiments, the catalytic cysteine residue of the E2 conjugating enzyme is at position 85, i.e. the E2 conjugating enzyme comprises a C85K mutation. In some embodiments, the catalytic cysteine residue of the E2 conjugating enzyme is at position 87, i.e. the E2 conjugating enzyme comprises a C87K mutation. Alternative methods to prevent dissociation of ubiquitin from E2 might involve the incorporation of unnatural lysine derivatives with progressively shorter aliphatic side chains (i.e. diamino propionic acid, diaminobutyric acid and ornithine)

Some E2 conjugating enzymes, such as UBE2D3, additionally comprise a serine residue capable of forming non-covalent bonds to ubiquitin. These interactions promote association of the ubiquitin of one conjugate molecule to the E2 conjugating enzyme of another conjugate molecule (self-association). In order to inhibit self-association of the conjugate molecules, the serine residue may be replaced with a residue that does not associate with ubiquitin, such as an arginine residue. In certain embodiments, the serine residue capable of forming non-covalent bonds to ubiquitin is at position 22, i.e. the E2 conjugating enzyme comprises a S22R mutation.

Some E2 conjugating enzymes, such as UBE2N, additionally comprise a native lysine residue capable of conjugating to ubiquitin, thus promoting conjugation of ubiquitin at the native residue rather than at the position of the catalytic cysteine residue or the former position of the catalytic cysteine residue (e.g. where the cysteine has been replaced with a more stable linker such as lysine). Self-association may also be promoted. To inhibit conjugation of ubiquitin at the native lysine residue, the native lysine residue may be replaced with a residue that does not associate with ubiquitin, such as an arginine residue. In certain embodiments, the native lysine residue is at position 92, i.e. the E2 conjugating enzyme comprises a K92A mutation.

The E2 conjugating enzyme may be any E2 enzyme capable of binding to ubiquitin. Typically, however, the E2 conjugating enzyme is UBE2D3. In some embodiments, the E2 conjugating enzyme is UBE2D3 or UBE2N.

In some embodiments, the E2 conjugating enzyme bears an N-terminal histidine tag, such as a hexahistidine tag. These tags facilitate purification of the conjugate molecules of the invention as well as aiding detection of the conjugate molecules via Western blot (a.k.a. immunoblot) analysis.

The conserved (and activity-dependent) consensus interaction of the Ub component within the closed E2-Ub, coupled with the enhanced free energy of binding for activated RING E3s, is exploited for the development of ABPs. The ABPs of the invention are effective in activity profiling RING E3 ligases, RING E1 ligases and deubiquitination enzymes in diverse sample types.

Therefore, in a third aspect, the invention provides use of the conjugated molecule of the second aspect in a method of activity profiling RING E3 enzymes, RING E1 enzymes and/or deubiquitinating enzymes. In one embodiment, use of the conjugated molecule of the second aspect is in a method of activity profiling RING E3 enzymes. In a further embodiment, the RING E3 enzyme is any one or a combination of RNF4, Cbl such as c-Cbl, Praja2, TRIM11, HECT (11), RBR (1) and RCR (1). For example, the RING E3 enzyme may be RNF4 or c-CBl. In some embodiments, the RING E3 enzyme is any one or a combination of RNF4, Cbl such as c-Cbl, Praja2, TRIM11, HECT (11), RBR (1), and RCR (1), TRAF6, TRAF2 and HLTF. For example, the RING E3 enzyme may be RNF4, c-CBl or TRAF6.

RING E3 enzymes are inactive in the monomeric state, predominant at endogenous concentrations. Activation of RING E3 enzymes may be achieved by RING dimerization, leading to ligase activity of the RING E3 enzyme (Rojas-Fernandez, A. et al., 2014, supra). Alternatively, monomeric RING E3 enzymes may be activated by non-RING elements (NREs), see for example Dou H. et al., 2013, supra. Activation of E3 enzymes leads to ubiquitination (see FIG. 1a), i.e. the active RING E3 enzyme binds to an E2-Ub (a conjugate comprising an E2 conjugating enzyme and ubiquitin) inducing a closed E2-Ub conformation.

An active RING E3 enzyme may bind to a conjugated molecule of the invention via the RING E3 or the NRE. On irradiation of the resulting complex, the photocrosslinker moiety of the conjugated molecule may covalently bond to the RING E3 or the NRE (see FIG. 1b). Thus, the conjugated molecule of the invention may act as a RING E3 ABP, wherein active RING E3 enzymes are detected and may be further characterized.

In a fourth aspect, the invention provides a method of detecting an interaction between the conjugate molecule of the second aspect and a RING E3 enzyme, RING E1 enzyme and/or deubiquitinating enzyme, the method comprising contacting the conjugate molecule of the second aspect with said RING E3 enzyme, RING E1 enzyme and/or deubiquitinating enzyme and detecting the formation of any new conjugates.

When used herein, "contacting" refers to any means allowing the conjugate molecule of the invention to interact with the RING E3/RING E1/deubiquitinating enzyme. Typically, contacting occurs in an aqueous solution comprising the conjugate molecule of the invention and a RING E3 enzyme.

On irradiation, the photocrosslinker moiety of the conjugated molecule may covalently bond to the RING E3/RING E1/deubiquitinating enzyme. If the conjugated molecule of the invention is unstable in the presence of photons, then the photocrosslinker moiety of the conjugated molecule may covalently bond to the enzyme on irradiation with photons of any frequency. However, if the conjugated molecule is stable in the presence of natural light, higher frequencies than natural light may be required for a covalent bond to form between the activated ubiquitin molecule and the enzyme. Typically, UV light, i.e. light with a wavelength within the range of 10 to 400 nm, is used to covalently link the photocrosslinker moiety to the enzyme.

The skilled person is aware that the irradiation time required for formation of a covalent bond between the enzyme and the conjugated molecule is dependent on various factors. For example, the irradiation time may be affected by the concentration of the sample to be irradiated (a more concentrated sample is likely to require a longer irradiation time); the frequency of light used to irradiate the sample (a frequency matching that absorbed by the photocrosslinker moiety is likely to require a shorter irradiation time); and the power of the radiation source (a greater power is likely to result in a shorter irradiation time). The conjugated molecule of the invention and the enzyme may be irradiated for 1 to 50 minutes. In some embodiments, the conjugated molecule of the invention and the enzyme are irradiated for 1 to 40 minutes. Typically, irradiation is for 1 to 30 minutes.

When the enzyme is a RING E3 enzyme, the conjugated molecule of the invention may be used in any study in which RING E3 enzyme detection is useful. This includes the study of RING E3 enzyme regulation; the discovery of novel RING E3 enzymes; inhibitor screening; inhibitor selectivity profiling and/or stabilization of enzymatic intermediates for structural studies.

New conjugates of the method of the invention may be detected using various methods including fluorescent microscopy (or the naked eye), electron microscopy, enzyme-linked immunosorbent assays (ELISAs), gel electrophoresis and/or Western blots. Often, combinations of analytical methods are used to detect new conjugates of the invention. The skilled person is aware that methods suitable for detection of the new conjugates of the invention differ depending on whether or not reporter tags have been employed, and the identity of any reporter tags. For example, gel electrophoresis may be used to separate new conjugates from sample mixtures according to their size and charge and may be useful irrespective of whether or not reporter tags are employed. However, fluorescent microscopy may be used to identify new conjugates only if the conjugated molecules of the invention comprise fluorescent reporter tags.

The conjugate molecules of the invention may interact with any active RING E3 enzyme, i.e. the uses and methods of the invention are not restricted to any particular type of RING E3 enzyme. However, in some embodiments, the RING E3 enzyme is a RNF4, Cbl such as c-Cbl, Praja2, TRIM11, HECT (11), RBR (1) and RCR (1) enzyme. In specific embodiments, the RING E3 enzyme is a c-Cbl enzyme. In some embodiments, the RING E3 enzyme is any one or a combination of RNF4, Cbl such as c-Cbl, Praja2, TRIM11, HECT (11), RBR (1), and RCR (1), TRAF6, TRAF2 and HLTF. For example, the RING E3 enzyme may be RNF4, c-CBl or TRAF6.

Any discussion herein of documents, acts, materials, devices, articles or the like is not to be taken as an admission that any or all of these matters form part of the prior art base or were common general knowledge in the field relevant to the present disclosure as it existed before the priority date of each claim of this application.

It will be appreciated by those skilled in the art that numerous variations and/or modifications may be made to the invention as described herein without departing from the scope of the invention as described. The present embodiments are therefore to be considered for descriptive purposes and are not restrictive, and are not limited to the extent of that described in the embodiment. The person skilled in the art is to understand that the present embodiments may be read alone, or in combination, and may be combined with any one or a combination of the features described herein.

The subject-matter of each patent and non-patent literature reference cited herein is hereby incorporated by reference in its entirety.

The invention may be further understood with regard to the following non-limiting clauses:

1. An activated ubiquitin molecule comprising a photocrosslinker moiety in place of a glutamine residue at position 31 and/or an aspartic acid residue at position 32 of ubiquitin.

2. The activated ubiquitin molecule of clause 1 wherein the photocrosslinker moiety is in place of a glutamine residue at position 31 or an aspartic acid residue at position 32 of ubiquitin.

3. The activated ubiquitin molecule of clause 1 wherein the photocrosslinker moiety is in place of a glutamine residue at position 31 of ubiquitin.

4. The activated ubiquitin molecule of any one of clauses 1 to 3 wherein the photocrosslinker moiety is an unnatural amino acid.

5. The activated ubiquitin molecule of clause 4 wherein the unnatural amino acid comprises any one or a combination selected from the group consisting of diarylketones, diazirines, arylazides, diaryl/heteroarylketones, diheteroarylketones, heteroarylazides and 2-aryl-5-carboxytetrazoles.

6. The activated ubiquitin molecule of clause 4 wherein the unnatural amino acid comprises one type of functional group selected from the group consisting of diarylketones, diazirines, arylazides, diaryl/heteroarylketones, diheteroarylketones, heteroarylazides and 2-aryl-5-carboxytetrazoles.

7. The activated ubiquitin molecule of clause 4 wherein the unnatural amino acid comprises any one functional group selected from the group consisting of diarylketones, diazirines, arylazides and 2-aryl-5-carboxytetrazoles.

8. The activated ubiquitin molecule of clause 4 wherein the unnatural amino acid comprises a diarylketone.

9. The activated ubiquitin molecule of any one of clauses 5 to 8 wherein the aryl is optionally substituted and may be selected from the group consisting of phenyl or naphthalenyl; the heteroaryl is optionally substituted and may be selected from the group consisting of indolyl, imidazolyl, pyridyl, thiophenyl and furanyl.

10. The activated ubiquitin molecule of any one of clauses 5 to 9 wherein the aryl or heteroaryl may be substituted at one or more carbon atoms with any one or a combination selected from the group consisting of $C_{1-4}$hydrocarbyls, $C_{1-4}$alkyloxy, $C_{1-4}$haloalkyls, hydroxy and halo.

11. The activated ubiquitin molecule of clause 10 wherein halo is fluoro.

12. The activated ubiquitin molecule of any one of clauses 5 to 9 wherein the aryl or heteroaryl is optionally substituted with any one or a combination selected from the group consisting of methyl, ethyl, propyl, butyl, methoxy, ethoxy, propoxy, butoxy, trifluoromethyl, hydroxy and fluoro.

13. The activated ubiquitin molecule of clause 4 wherein the unnatural amino acid comprises a diarylketone selected from the group consisting of benzophenone, methylbenzophenone, dimethylbenzophenone, methoxybenzophenone, dimethoxybenzophenone, tertbutoxybenzophenone, ditertbutoxybenzophenone, trifluoromethylbenzophenone, di(trifluoromethyl)benzophenone, tetrakis(trifluoromethyl)benzophenone, hydroxybenzophenone, dihydroxybenzophenone, trihydroxybenzophenone, fluorobenzophenone, difluorobenzophenone and trifluorobenzophenone 14. The activated ubiquitin molecule of clause 4 wherein the unnatural amino acid comprises benzophenone.

15. The activated ubiquitin molecule of any one of clauses 4 to 14 wherein the unnatural amino acid is derived from any one of the group consisting of phenylalanine, tryptophan and histidine.

16. The activated ubiquitin molecule of any one of clauses 4 to 14 wherein the unnatural amino acid is derived from phenylalanine.

17. The activated ubiquitin molecule of any one of clauses 1 to 3 wherein the photocrosslinker moiety is p-benzoyl-L-phenylalanine.

18. The activated ubiquitin molecule of any one of clauses 1 to 17 wherein the ubiquitin is from an animal.

19. The activated ubiquitin molecule of any one of clauses 1 to 17 wherein the ubiquitin is from a mammal.

20. The activated ubiquitin molecule of any one of clauses 1 to 17 wherein the ubiquitin is from a human.

21. The activated ubiquitin molecule of any one of clauses 1 to 20 further comprising a reporter tag.

22. The activated ubiquitin molecule of clause 21 wherein the reporter tag comprises any one or a combination selected from the group consisting of biotin, epitopes and fluorophores.

23. The activated ubiquitin molecule of clause 22 wherein:
(i) the epitope is any one or a combination selected from Myc-tag, HA-tag, FLAG-tag, GST-tag, 6×His, V5-tag and OLLAS; and (ii) the fluorophore is any one or a combination selected from fluorescein, optimized S65T mutant, enhanced green fluorescent protein (EGFP), the monomeric A206K mutant, superfolder GFP (sfGFP), Emerald, TagBFP, mCerulean3, mCitrine/mVenus, tdTomato, mCherry, mApple, mKate2 and mNeptune, FLAsH-EDT2 and ReAsH-EDT2.

24. The activated ubiquitin molecule of clause 21 wherein the reporter tag is a biotin moiety.

25. The activated ubiquitin molecule of clause 24 wherein the biotin moiety is covalently linked to the ubiquitin or activated ubiquitin molecule via a terminal cysteine-, serine-, threonine- or tyrosine-containing motif.

26. The activated ubiquitin molecule of clause 25 wherein the terminal motif is N-terminal.

27. The activated ubiquitin molecule of clause 25 wherein the terminal motif is an N-terminal cysteine-containing motif.

28. The activated ubiquitin molecule of any one of clauses 25 to 27 wherein the terminal motif has the sequence MGCSSG.

29. A conjugate molecule comprising the activated ubiquitin molecule according to any one preceding clause conjugated to an E2 conjugating enzyme.

30. The conjugate molecule of clause 29 wherein the E2 conjugating enzyme comprises a lysine residue in place of the catalytic cysteine residue.

31. The conjugate molecule of clause 29 wherein the E2 conjugating enzyme comprises a C85K or C87K mutation.

32. The conjugate molecule of any one of clauses 29 to 31 wherein a serine or lysine residue capable of forming non-covalent bonds to ubiquitin is replaced with an arginine residue.

33. The conjugate molecule of any one of clauses 29 to 30 wherein the E2 conjugating enzyme comprises a C85K and a S22R mutation.

34. The conjugate molecule of any one of clauses 29 to 33 wherein the E2 conjugating enzyme is UBE2D3.

35. The conjugate molecule of any one of clauses 29 to 30, wherein the E2 conjugating enzyme comprises a C87K and a K92A mutation.

36. The conjugate molecule of any one of clauses 29 to 32 and 35, wherein the E2 conjugating enzyme is UBE2N.

37. The conjugate molecule of any one of clauses 29 to 36 wherein the E2 conjugating enzyme bears an N-terminal histidine tag.

38. The conjugate molecule of any one of clauses 29 to 36 wherein the E2 conjugating enzyme bears a hexahistidine tag.

39. Use of the conjugated molecule of any one of clauses 29 to 38 in a method of activity profiling RING E3 enzymes, RING E1 enzymes and/or deubiquitinating enzymes.

40. Use of clause 39 wherein the RING E3 enzyme is any one or a combination of RNF4, Cbl such as c-Cbl, Praja2, TRIM11, HECT (11), RBR (1), RCR (1), TRAF6, TRAF2 and HLTF, and the deubiquitinating enzyme is DUBs (31).

41. Use according to clause 39 or clause 40, wherein activity profiling is of a RING E3 enzyme.

42. The use of clause 41 for:
 (i) the study of RING E3 enzyme regulation;
 (ii) the discovery of novel RING E3 enzymes;
 (iii) inhibitor screening;
 (iv) inhibitor selectivity profiling; and/or
 (v) stabilization of enzymatic intermediates for structural studies.

43. A method of detecting an interaction between the conjugate molecule of any one of clauses 29 to 38 and a RING E3 enzyme, RING E1 enzyme and/or deubiquitinating enzyme, the method comprising contacting the conjugate molecule with said RING E3 enzyme, RING E1 enzyme and/or deubiquitinating enzyme and detecting the formation of any new conjugates.

44. The method of clause 43 wherein the RING E3 enzyme is any one or a combination of RNF4, Cbl such as c-Cbl, Praja2, TRIM11, HECT (11), RBR (1), RCR (1), TRAF6, TRAF2 and HLTF, and the deubiquitinating enzyme is DUBs (31).

45. The method of clause 43 or 44 wherein interaction is with a RING E3 enzyme.

46. The method of any one of clauses 43 to 45 further comprising irradiating the conjugate molecule and RING E3/RING E1/deubiquitinating enzyme such that the photo-crosslinker moiety of the conjugate molecule is covalently bonded to said RING E3/RING E1/deubiquitinating enzyme.

47. The method of clause 46 wherein irradiation is with UV light.

48. The method of clause 47 wherein the UV light has a wavelength within the range of 200 to 400 nm.

49. The method of any one of clauses 45 to 48 wherein the RING E3 enzyme is a RNF4, Cbl or TRAF6 enzyme.

50. The method of clause 49 wherein the Cbl enzyme is a c-Cbl enzyme.

The invention is further described by the following non-limiting examples.

Examples

Activity-dependent profiling of two cancer-associated RING E3s, RNF4 and c-Cbl, is demonstrated in response to their native activation signals. RNF4 is activated by poly-SUMO chain-induced dimerization whereas c-Cbl is activated by tyrosine phosphorylation. Combining biotin reporter tagged conjugates with mass spectrometry, it is demonstrated that parallelized measurement of native cellular RING E3 activity can carried out, Furthermore, cellular activation of distinct RING E3s can be identified upon cellular perturbation (e.g. growth factor stimulation). The conjugate molecules of the invention have the potential to advance E3 ligase research and the development of selective modulators against this enzyme class.

Material and Methods

Experimental Model and Subject Details
H293T cells were obtained from ATCC. 293T is a human cell line, derived from the HEK293 cell line, that expresses a mutant version of the SV40 large T antigen (RRID: CVCL_0063). Cells were cultured at 37° C. in a humidified incubator under a 5% $CO_2$ atmosphere. Dulbecco's modified Eagle medium was used and supplemented with fetal bovine serum and L-glutamine. BL21(DE3) and *Escherichia coli* BL21 Rosetta™ (DE3) cells used for protein expression in this study were grown in 1 L flasks each containing 1 L LB media supplemented with 100 mL$^{-1}$ of ampicillin and 34 mL$^{-1}$ chloramphenicol (for details see STAR Methods—Expression of Recombinant Proteins).

Methods Details
Site-Specific Incorporation of pBpa Unnatural Amino Acid into Ubiquitin
pEvol-Bpa plasmid was derived from pEVOL-pBoF (kindly provided by P. Schultz, The Scripps Research Institute). Mutations for incorporation of Bpa were introduced into both copies of MjYRS gene to make the plasmid pEVOL-Bpa (Young et al., 2010; Chin et al., 2002). BL21 cells (50 µL) were co-transformed with the pET-Ubiquitin-6His-TAGx (where x is the Bpa incorporation site) and pEvol-Bpa plasmids using heat shock and recovered in 200 µL SOC media at 37° C. for 1 hour and used to inoculate 50 mL Luria-Bertani (LB) containing 100 µg mL$^{-1}$ ampicillin and 34 µg mL$^{-1}$ chloramphenicol. 10 mL overnight culture was then used to inoculate 1 L LB broth containing the same concentrations of antibiotics. The cells were grown until $OD_{600}$ reached ~0.6 and the culture was divided into two 500 mL portions. One portion was supplemented with 1 mM p-Benzoyl-L-phenylalanine (Bpa; Bachem) and the other served as a control where Bpa was withheld. The cultures were incubated for 20 mins (37° C., 200 rpm), or until the $OD_{600}$ reached 0.6-0.7, and protein expression was induced by adding 0.02% arabinose and 1 mM isopropyl β-D-1-thiogalactopyranoside (IPTG). The cultures were incubated for 5 hours (37° C., 200 rpm). The cells were harvested and suspended in 10 mL BugBuster® Protein Extraction (Merk Millipore) reagent before transferring to 50 mL falcon tube. The lysates were incubated for 20 minutes and then clarified by centrifugation before transferring to 50 mL falcon tube containing 1 mL Ni-NTA agarose beads and incubated for 1 hour with gentle shaking. The resin was centrifuged (4° C., 1000 rpm) and washed with wash buffer (20 mM $Na_2HPO_4$, pH 7.5, 25 mM imidazole). Finally, the protein was eluted with 200 µL elution buffer (20 mM $Na_2HPO_4$, pH 7.5, 300 mM imidazole). A 20 µL aliquot from the elution fraction was mixed with equal amount of 4×SDS loading buffer and loaded onto 4-12% SDS-PAGE gel. The proteins were separated at 200 V using MES buffer for 30 minutes and detected using Coomassie blue staining. A separate 20 µL protein was analyzed by LC-MS. LC-MS was carried out with an Agilent 1200 LC-MS system fitted with a Max-Light Cartridge flow cell coupled to a 6130 Quadrupole spectrometer. An Agilent ZORBAX 300SB-C3 5 µm, 2.1×150 mm column was employed unless otherwise stated. The solvent system consisted of 0.05% trifluoroacetic acid in $H_2O$ as buffer A, and 0.04% TFA acid in acetonitrile as buffer B. Protein UV absorbance was monitored at 214 and 280 nm. MS acquisition was carried out in positive ion mode and total protein masses were calculated by deconvolution within the MS Chemstation software (Agilent Technologies). Fractions containing the pBpa incorporated-Ub were pooled concentrated with an Amicon Ultra-15 3 kDa MWCO centrifugal filter device (Millipore). The sample was desalted into 10 mM Tris-HCl pH 7.5 using a PD-10 column (GE Life Sciences). DTT (1 mM) was added to the sample, followed by hexahistidine tag cleavage with UCH-L3 (Virdee et al., 2010), at a final concentration of 15 µg mL$^{-1}$. The sample was incubated at 37° C. for 2 hours to remove the N-terminal His tag. Bpa incorporated-Ub was further purified by semi-preparative HPLC and the fractions were lyophilized yielding approximately 8-10 mg of Ub-pBpa.

Expression of UBE2D3(S22R/C85K) Recombinant Protein

S22R and C85K were introduced into UBE2D3 by using site-directed mutagenesis. The cells were grown until $OD_{600}$ reached 0.6-0.7 at 37° C., 200 rpm. Once $OD_{600}$ reached 0.6~0.7, protein expression was induced by adding IPTG (1 mM) and incubated at 37° C. for 3 h. The cells were harvested and resuspended in buffer (20 mM Na2HPO4, pH 7.5, 150 mM NaCl, 1 mM TCEP, complete protease inhibitor cocktail (EDTA-free, Roche). Lysozyme was added (0.5 mg mL$^{-1}$) and cells were incubated on ice for 30 min followed by sonication. Clarified lysates containing His6-tagged UBE2D3(S22R/C85K) were loaded onto Ni-NTA resin and washed with buffer (20 mM pH 7.5, $Na_2HPO_4$, pH 7.5, 25 mM imidazole, 150 mM NaCl, 1 mM TCEP), followed by elution with elution buffer (20 mM pH 7.5, $Na_2HPO_4$, pH 7.5, 300 mM imidazole, 150 mM NaCl, 1 mM TCEP). Samples were further purified by size-exclusion chromatography with a HiLoad Superdex-75 16/60 column (GE Healthcare) with running buffer (20 mM $Na_2HPO_4$, pH 7.5, 150 mM NaCl, 1 mM TCEP).

Preparation of Biotin-UbBpa31

Lyophilized UbBpa31 with an N-terminal MGCSSG cysteine-containing motif (10 mg) was reconstituted in 1 mL 10% DMSO/90% 0.5 mM TCEP (aq) and incubated at 23° C. for 45 mins with gentle mixing, followed by the addition of 5 molar equivalents of EZ-link iodo-acetyl PEG2-Biotin (Thermofisher) in reaction buffer (50 mM $Na_2HPO_4$, 150 mM NaCl, 0.5 mM TCEP). The reaction was incubated at 23° C. with gentle shaking for 1 h and monitored to completion by LC-MS. Product was then purified by preparative HPLC at a flow rate and lyophilized yielding biotin-UbBpa31 (6-8 mg).

Preparation of Isopeptide-Linked photoABPs

To generate the UBE2D3(S22R/C85K)-UbBpa, UBE2D3 (S22R/C85K) (200 µM) was incubated with UbBpa (200 µM) and $His_6$-Uba1 (1 µM) at 35° C. for 26 h conjugation buffer (50 mM Tris, pH 10.0, 150 mM NaCl, 3 mM ATP, 5 mM $MgCl_2$, 1 mM TCEP). The E2-UbBpa conjugate was applied onto a HiLoad 16/60 Superdex 75 gel filtration column (GE Healthcare) (20 mM HEPES, pH 7.5, 150 mM NaCl, 1 mM TCEP). The purified UBE2D3(S22R/C85K)-UbBpa conjugate was concentrated to 2 mg ml$^{-1}$, and stored at −80° C. Biotin-photoABP probe was prepared using the same procedure.

Expression of Recombinant RNF4 Protein.

Cloning, expression and purification of linear fusion of two RNF4 RING domains, and associated mutants, has been described previously (Plechanovova et al., 2011). The fusion of two RING domain of RNF4 were expressed in E. coli Rosetta (DE3) cells (Novagen). The cells were grown until $OD_{600}$ reached 0.6~0.7 at 37° C., 200 rpm. Once the $OD_{600}$ reached 0.6-0.7, the protein expression was induced by adding IPTG (1 mM) and incubated overnight at 16° C., 200 rpm.

The cells were harvested and resuspended in lysis buffer (50 mM Tris, pH 7.5, 0.5 M NaCl, 10 mM imidazole, 2 mM benzamidine, complete protease inhibitor cocktail (EDTA-free, Roche)) and cells were lysed by sonication. His6-MBP-fusion proteins were purified by Ni-NTA (Qiagen) chromatography, followed by cleavage with TEV protease at 4° C. overnight. To remove any uncleaved fusion protein, His6-tagged MBP, as well as His6-tagged TEV protease, material was depleted against fresh Ni-NTA resin followed by size-exclusion chromatography with a HiLoad Superdex 75 16/60 column (GE Healthcare) (20 mM Tris, 150 mM NaCl, 1 mM TCEP, pH 7.5).

Expression of c-Cbl and c-Cbl (Y371F) Recombinant Protein

BL21(DE3) cells (50 µL) were transformed with the pGEX6P-1-Cbl plasmid and recovered in 200 µL SOC media at 37° C. for 1 hour and used to inoculate 50 mL Luria-Bertani (LB) containing 100 µg mL$^{-1}$ ampicillin. 10 mL overnight culture was then used to inoculate LB broth containing the same concentration of antibiotic and 0.2 mM zinc chloride. The cells were grown until $OD_{600}$ reached 0.6-0.7 at 37° C., 200 rpm. Once the $OD_{600}$ reached 0.6~0.7, protein expression was induced by adding 1 mM IPTG and left overnight at 16° C., 200 rpm. The cells were harvested and resuspended in buffer (50 mM Hepes, pH 7.5, 0.5 M NaCl, 1 mM TCEP) and lysed by sonication. The lysates were incubated with glutathione sepharose beads for 1 hour with gentle shaking. The resin was centrifuged (4° C., 1000 rpm) and washed with buffer (50 mM HEPES, pH 7.5, 150 mM NaCl, 1 mM TCEP), followed by cleavage with Rhinovirus 3C protease at 4° C. overnight. Cleaved protein was further purified by size-exclusion chromatography with a HiLoad Superdex 200 16/600 column (GE Healthcare) (20 mM HEPES, 150 mM NaCl, 1 mM TCEP, pH 7.5).

c-Cbl Phosphorylation

Purified c-Cbl (3 µM) was phosphorylated by incubating with Src kinase (1.5 µM), 10 mM $MgCl_2$, 5 mM ATP at 37° C., 45 mins. Samples (15 µl) were collected and mixed well with 4×LDS loading buffer (ThermoFisher), followed by boiling before loading onto 7.5% acrylamide phos-tag gel. The proteins were separated at 160 V using MOPS buffer for 60 mins and analysed using Coomassie staining and western blot.

Furthermore, ATP-dependent phosphorylation and photo-cross linking of c-Cbl with photoABP-UbBpa31 (5 µM) was analysed using Coomassie staining. Samples (15 µl) were collected and mixed well with 4×LDS loading buffer, followed by boiling them for 5 mins at 95° C. before loading onto 4-12% SDS-PAGE gel using MOPS running buffer and analysed using Coomassie staining. Moreover, gels were blotted and analysed using western blot with anti-Cbl (1:5000 dilution) as primary and anti-mouse (1:10000 dilution) as secondary antibodies.

UV Irradiation Conditions for Photo-Cross-Linking

Photo-cross linking reactions (45 µL) were performed in a 24-well plate (Cryshem HR3-158, Hampton Research) in reaction buffer (20 mM HEPES, pH 7.5, 150 mM NaCl, 1 mM TCEP). Samples were divided into two portions. One portion was irradiated at 365 nm on ice at a distance of 2 cm from a handled UV lamp (BLE-8T365, Spectroline), for 10-30 min and the other portion was preserved in the dark. For purified proteins such as RNF4-RING (5-50 µM), c-Cbl (3 µM) and c-Cbl Y371F (3 µM), photo-cross linking reactions were performed with photoABP-UbBpa31 probe (5-50 µM) and irradiated with UV. Samples were resolved by SDS-PAGE and visualized by Coomassie staining or immunoblotting. Control experiments were performed under the same conditions.

Photo-Crosslinking in Cell Extracts

HEK293 cells were transfected with plasmids expressing GFP-Cbl, GST-Src and GFP-Cbl. The cells were lysed in lysis buffer (50 mM $Na_2HPO_4$, 10 mM Glycerophosphate, 50 mM Sodium Fluoride, 5 mM Sodium Pyrophosphate, 1 mM Sodium Vanadate, 0.25 M Sucrose, 50 mM NaCl, 0.2 mM PMSF, 1 mM Benzamidine, 10 µM TCEP, 1% NP-40). Probe photoABP-Bpa31 (25 µM) was mixed with cell lysate and UV irradiated (10 mins) using the photocrosslinking procedure described in the general method. Samples were analysed by 4-12% SDS-PAGE gel using MOPS running buffer (160 V, 60 mins) and visualized by immunoblotting with anti-Cbl (1:5000 dilution) as primary and anti-mouse (1:10000 dilution) as secondary antibodies.

Phos-Tag™ Gel Electrophoresis

To assess Src-mediated c-Cbl phosphorylation, we poured resolving gels (7.5% acrylamide/bis-acrylamide, 375 mM Tris-HCl pH 8.8, 0.1% sodium dodecyl sulfate (SDS), 100 µM $MnCl_2$, 50 µM Phos-Tag™, 0.05% (w/v) ammonium persulphate (APS), 0.0625% (v/v) tetramethylethylenediamine (TEMED)) and stacking gels (4% acrylamide/bis-acrylamide, 125 mM Tris-HCl pH 6.6, 0.1% SDS, 0.05% (w/v) APS, 0.1% (v/v) TEMED), degassing with argon, then allowing polymerization at room temperature for three hours. Cell extracts (50 µg) were boiled in LDS-sample buffer and supplemented with 10 mM $MnCl_2$ before loading. Electrophoresis was performed at 70 V through the stacking gel and 130 V through the resolving gel using running buffer (25 mM Tris-HCl, 192 mM Glycine, 0.1% SDS), before staining with Coomassie dye, or washing 3×20 min in transfer buffer (48 mM Tris-HCl, 39 mM glycine, 20% methanol) supplemented with 10 mM EDTA and 0.05% SDS to chelate manganese, followed by 1×20 min in transfer buffer supplemented with 0.05% SDS. Protein was then transferred to 0.45 µm nitrocellulose membrane in transfer buffer at 100 V, 3 hr, 4° C.

Cell Culture, Transfection and Lysis 293T cells were cultured (37° C., 5% $CO_2$) in Dulbecco's modified Eagle's medium (DMEM) supplemented with 10% (v/v) fetal bovine serum (FBS), 2.0 mM L-glutamine and antibiotics (100 units $mL^{-1}$ penicillin, 0.1 mg $mL^{-1}$ streptomycin). Cells were seeded at a density of $4 \times 10^6$ in 100 mm dishes. 18 hr post seeding, cell transfections (2 µg DNA, empty vector (pcDNA (Thermo Fisher)), pcDNA and GST-Src, pcDNA and GFP-c-Cbl, or GST-Src and GFP-c-Cbl) were performed using 5 µL Fugene-6 (Promega) in 200 µL Eagle's Minimum Essential Medium (Opti-MEM). MG132 (25 µM) was added to cells 90 min before harvesting. Cells were rinsed and collected with ice-cold PBS, and extracted with ice-cold lysis buffer (50 mM Tris-HCl pH 7.5, 10 mM sodium 2-glycerophosphate, 50 mM sodium fluoride, 5.0 mM sodium pyrophosphate, 1.0 mM sodium orthovanadate, 0.27 M sucrose, 50 mM NaCl, 0.2 mM phenylmethanesulfonyl fluoride (PMSF), 1.0 mM benzamidine, 10 µM TCEP, 1% NP-40) on ice for 30 min. Lysates were clarified by centrifugation at 4° C. for 20 min at 21,100 g. Supernatants were collected and protein concentration was determined by Bradford assay.

Activity-Based Proteomic Profiling of EGF-Stimulated HEK293 Cells 293T cells were seeded in 150 mm dishes at a density of $5 \times 10^6$ and cultured (37° C., 5% $CO_2$) in Dulbecco's modified Eagle's medium (DMEM) supplemented with 10% (v/v) fetal bovine serum (FBS), 2.0 mM L-glutamine and antibiotics (100 units $mL^{-1}$ penicillin, 0.1 $mgmL^{-1}$ streptomycin). The next day, media was replaced for DMEM lacking FBS. The following day, cells were treated with 20 µM MG132 and 200 nM Bafilomycin for 6 hours at 37° C., then with or without recombinant EGF 100 $ngmL^{-1}$ (Thermo Fisher Scientific, PHG0311) for 15 minutes at 37° C. Dishes were transferred on to ice, washed, resuspended in ice-cold PBS, and washed twice at 4° C., and lysates extracted in ice-cold lysis buffer. 293T cells were treated with biotinylated probe (biotin-photoABP-UbBpa31) (20 µM). Samples were divided and irradiated with UV for 1 hour or UV was withheld. Biotin enrichment was then carried out against streptavidin resin followed by on-resin tryptic digestion and LC-MS/MS analysis and data processing, as previously described (Pao et al., 2018, supra).

Results

Design and Assembly of Photocrosslinking RING ABPs

Figure 7:
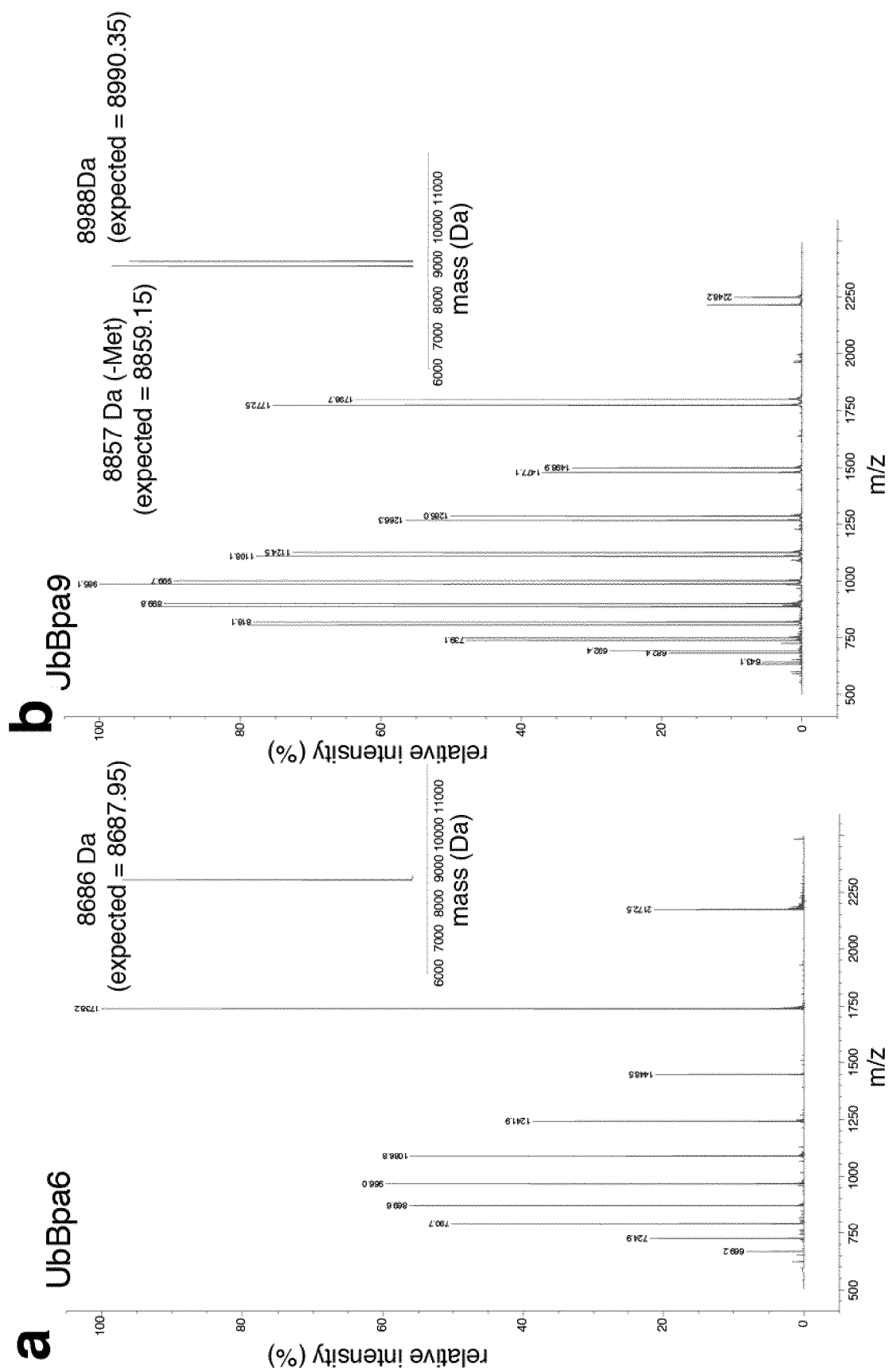
Figure 7:
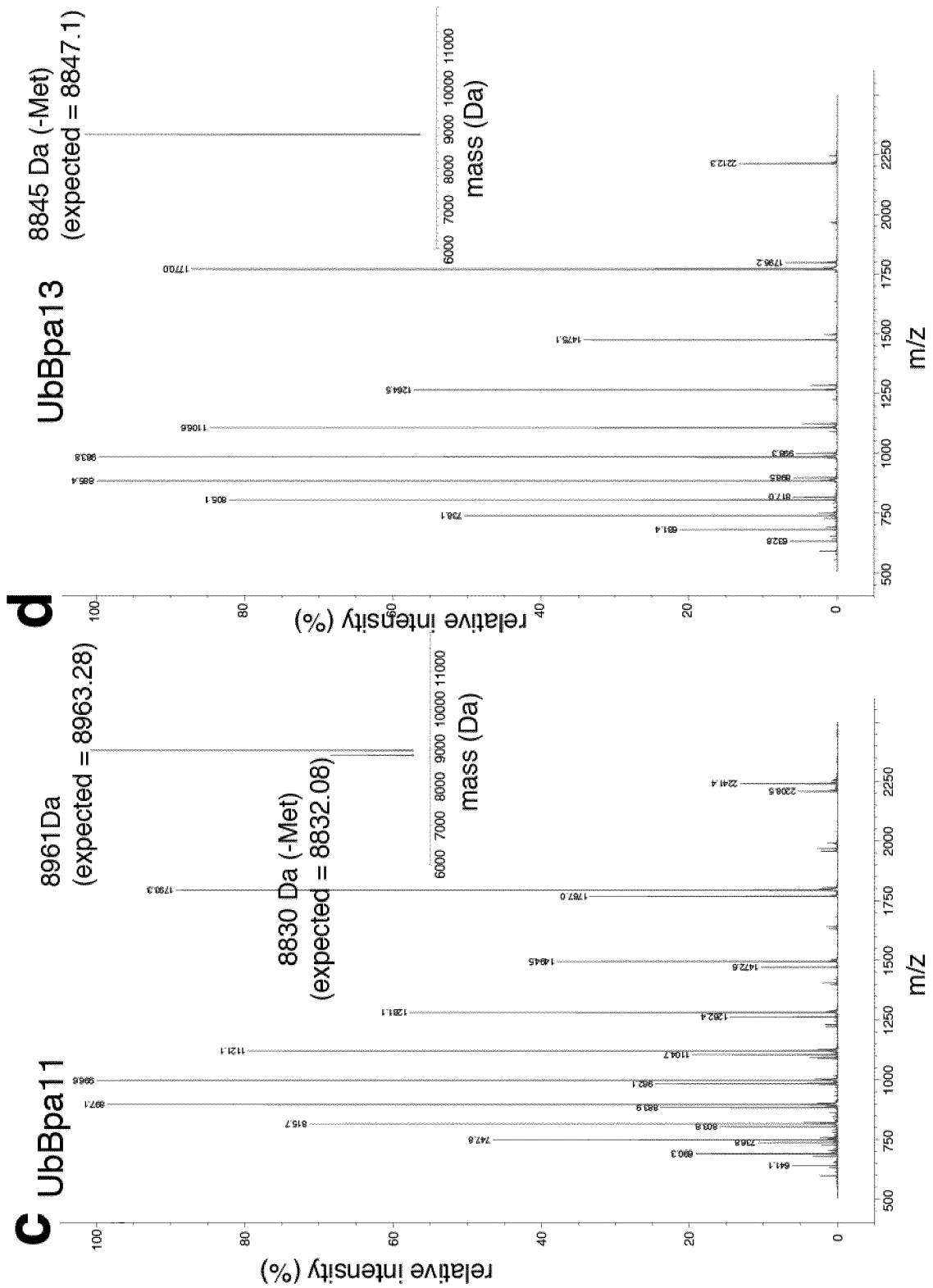
Figure 7:
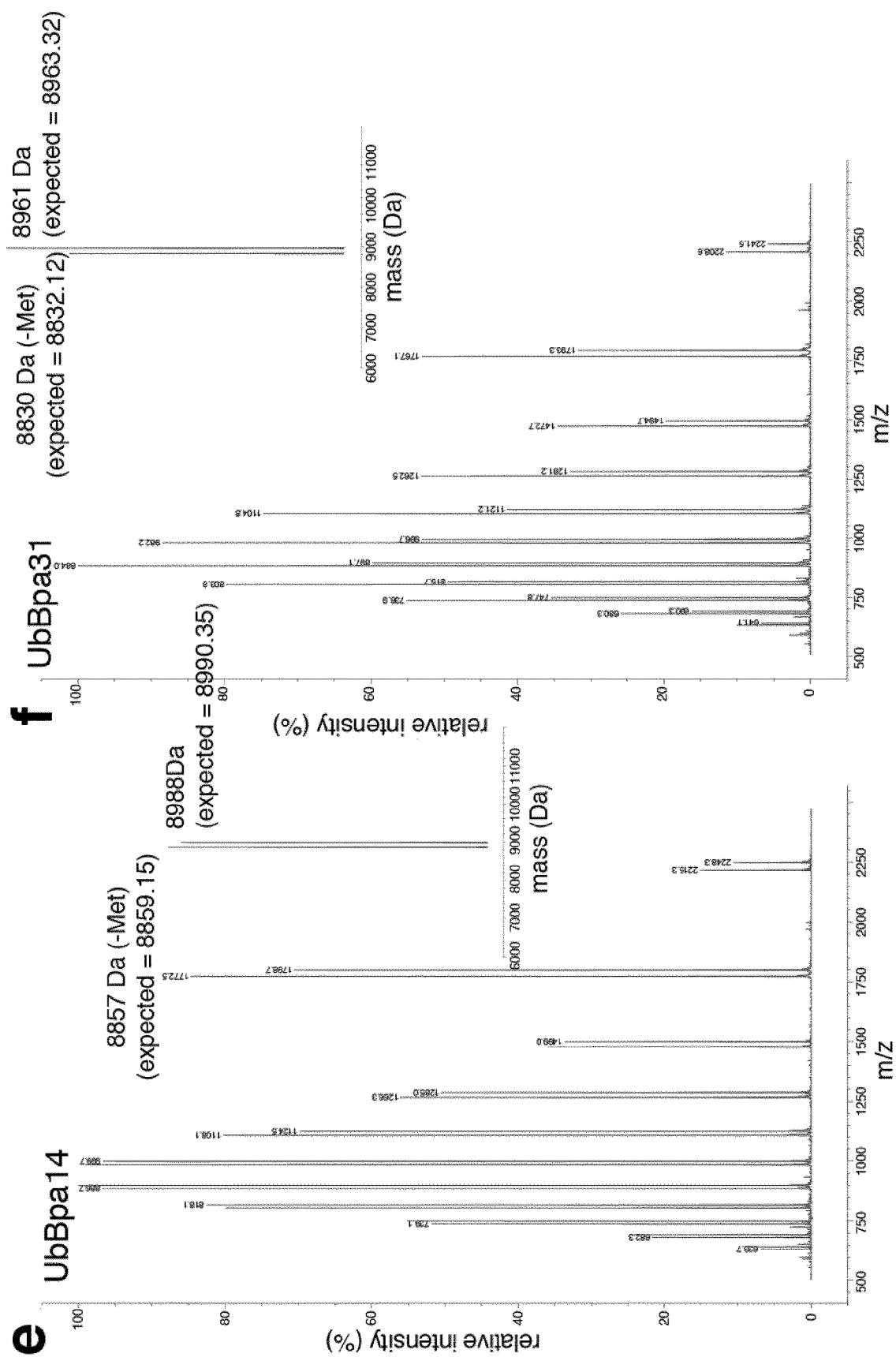
Figure 7:
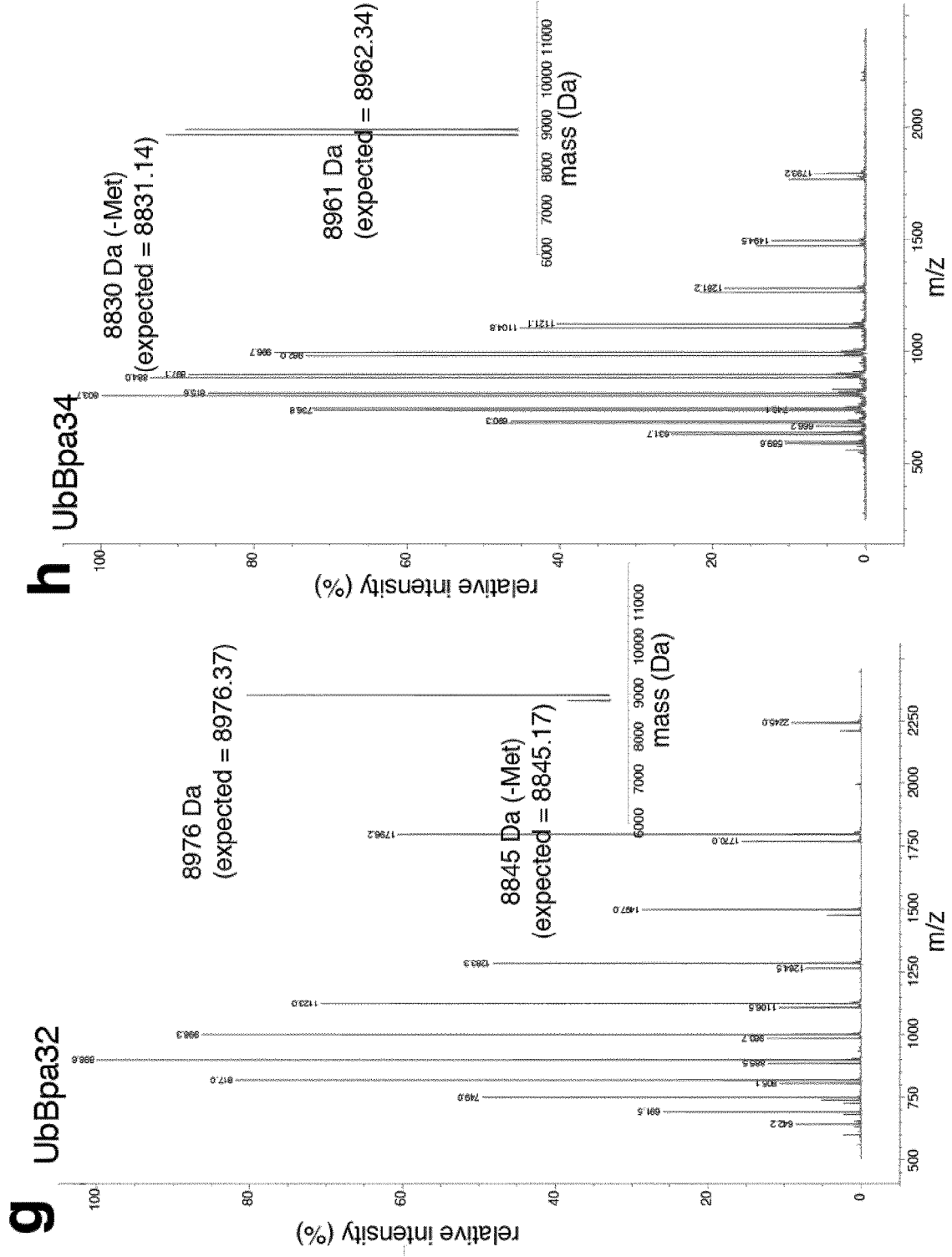
Figure 7:
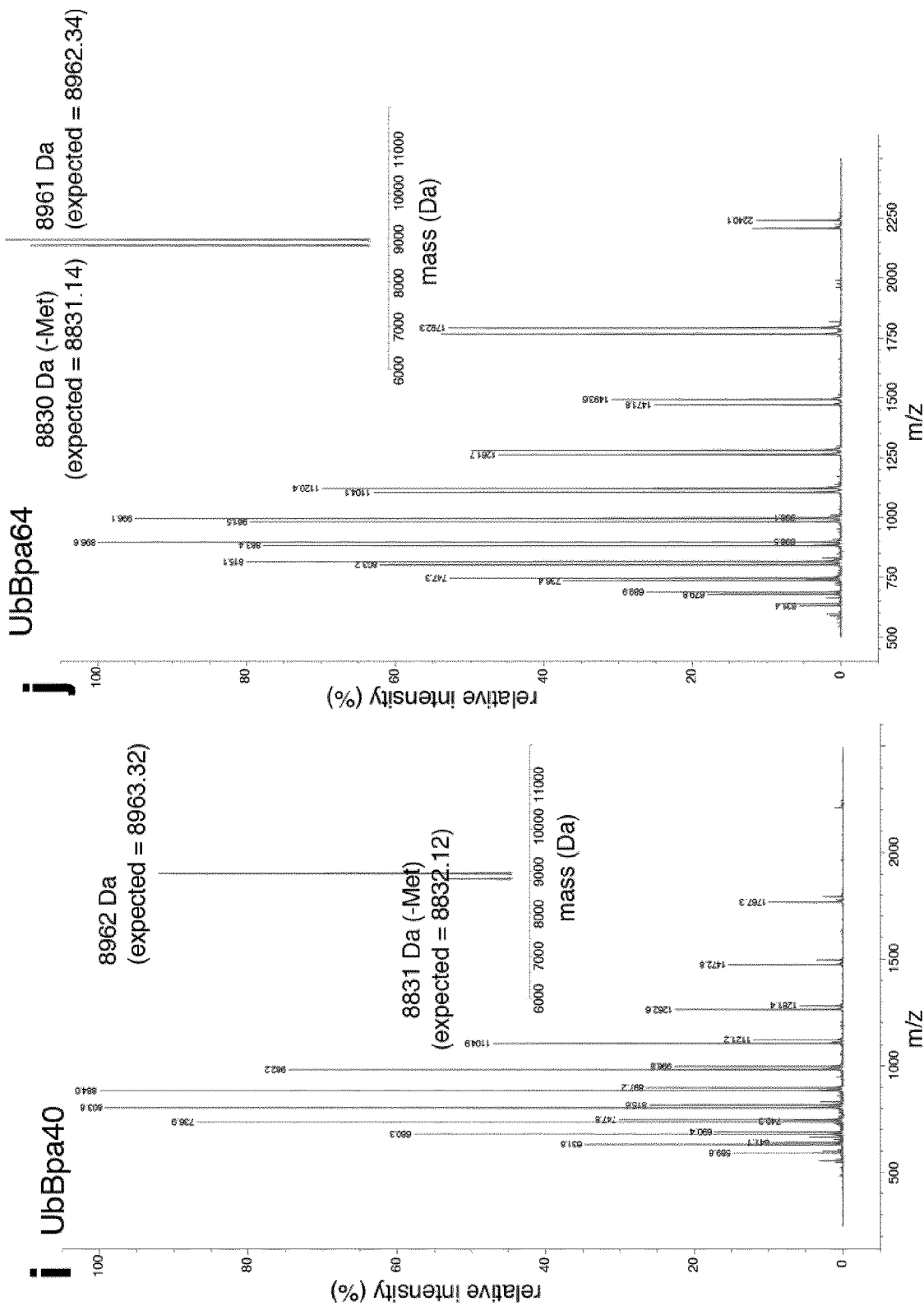
Figure 7:
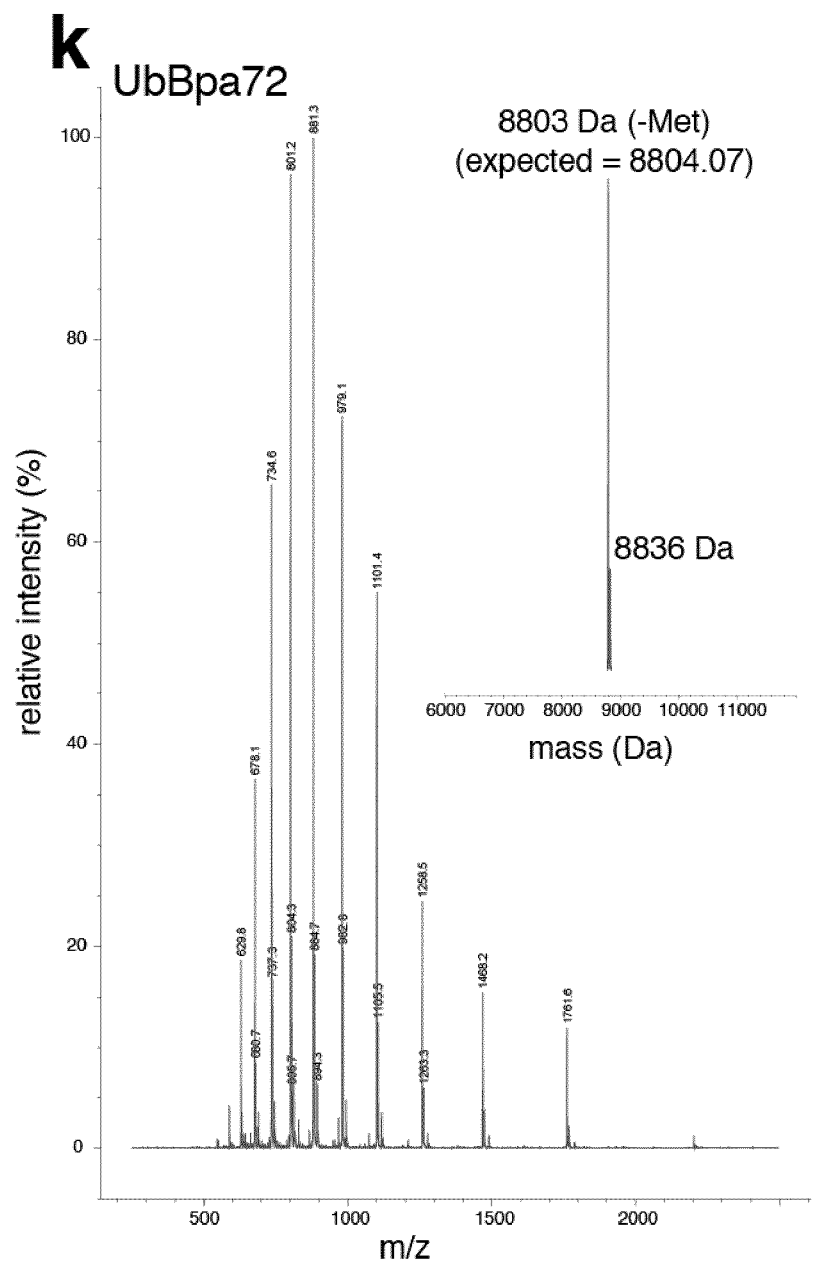

To establish potential positions for photocrosslinker incorporation we generated structural superpositions for solved RING E3:E2~Ub cocrystal structures (FIG. 5) (Dou et al., 2012b, 2013; Koliopoulos et al., 2016; Plechanovova et al., 2012, supra). Striking conservation in binding mode was apparent and multiple residues within both Ub and E2 lie proximal to the RING domain(s). To impart activity-dependence to the probe we incorporated the photocrosslinking moiety into Ub as this component only binds proximally to active RING E3s. We chose 10 consensus sites within Ub that are proximal to activated RINGs (FIG. 1c) and incorporated the photocrosslinking amino acid p-benzoyl-L-phenylalanine (Bpa) using an evolved Methanocoldococcus Janashi tyrosyl-Trna synthetase-Trna$_{CUA}$ pair (FIG. 1b, c) (Chin et al., 2002, supra). Efficient incorporation was achieved at all sites yielding ~4-6 mg of protein per litre of culture medium. Ub mutants were purified to homogeneity and characterized by LC-MS (FIGS. 6 and 7). All of the mutant Ub variants were then enzymatically conjugated to the promiscuous E2 UBE2D3 (Brzovic, P. S. et al. (2006). Mol Cell 21, 873-880) bearing an N-terminal hexahistidine tag (FIG. 1d). In addition to facilitating purification, the latter serves as a convenient reporter for immunoblot analysis. Conjugation to E2 was carried out with E1 activating enzyme and to form a more stable linkage between Ub and E2 the catalytic cysteine was mutated to lysine enabling stable isopeptide conjugation (Plechanovova et al., 2012, supra) (FIG. 2a). Importantly, structural analysis has shown that the isopeptide is an acceptable structural mimetic of the native thioester (Koliopoulos et al., 2016; Plechanovova et al., 2012; Wright et al., 2016, supra). We also introduced an S22R mutation into the E2 component which disrupts a non-covalent Ub binding site that could result in ABP self-association (Brzovic, P. S., and Klevit, R. E. (2006). Cell Cycle, 5, 2867-2873). All E2~Ub variants were purified to homogeneity by size exclusion chromatography as determined by SDS-PAGE and LC-MS analysis (FIGS. 2b-d & 8).

Activity-Dependent Profiling of the Dimeric RING E3 RNF4

The RING E3 RNF4 is inactive in the monomeric state, which is predominant at endogenous concentrations. Binding of poly-SUMO chains to SUMO Interacting Motifs (SIMs) within RNF4 enhances the local concentration of RNF4 thereby promoting RING domain homodimerization and activation of E3 ligase activity (Rojas-Fernandez et al., 2014, supra). This leads to ubiquitination and degradation of SUMO modified promyelocytic leukemia protein (PML) (Tatham, M. H. et al (2008). Nat Cell Biol, 10, 538-546). Strikingly, therapeutic induction of this process leads to remission of acute promyelocytic leukemia in >90% of cases (Massaro, F., Molica, M., and Breccia, M. (2016). Int J Hematol Oncol, 5, 105-118). An engineered version of RNF4 that is constitutively active has been designed that consists of full-length protein with an additional RING domain fused to the native C-terminus via a flexible linker (RNF4-RING) (FIG. 3a) (Plechanovova et al., 2011, supra). To determine the optimum photocrosslinker position we incubated all 10 Bpa mutant E2~Ub conjugates with RNF4-RING (FIG. 9) and assessed crosslinking efficiency upon UV irradiation (10 min). Significant and dose responsive crosslinking was only observed with Bpa incorporation at position 31 (photoABP-UbBpa31) (FIGS. 3b and 10). Importantly, no crosslinking was observed when RNF4-RING was incubated and UV irradiated with unconjugated UbBpa31 indicating that the photocrosslinking was dependent on E2-driven Ub proximity, consistent with the native mechanism. Notably, an additional crosslinking product corresponding to the molecular weight for the addition of two photoABP-UbBpa31 molecules was observed (FIG. 3b). Structural studies on dimeric RING:E2~Ub complexes has revealed that both faces of the active RING dimer engage and activate a separate E2~Ub conjugate (FIG. 3c). By virtue of the fused RNF4-RING construct it is possible to disrupt binding to a single E2~Ub molecule or both by introducing an M140A R181A double mutation into one or both of the RING domains (RNF4x-RING or RNF4x-RINGx, respectively) (Rojas-Fernandez et al., 2014, supra). Consistent with photoABP-UbBpa31 profiling this structurally elucidated bipartite mechanism, crosslinking of the second E2~UbBpa31 molecule was lost with RNF4x-RING and was completely abolished with RNF4x-RINGx (FIG. 3d). To further confirm activity-dependent photocrosslinking we prepared a mutant photoABP-UbBpa31 control probe. Part of the conserved E2-RING interaction involves the E2 F62 residue (F63 in some model E2s) and mutation to alanine typically impairs/abolishes E3 binding (Weissman, A. M. (2001). Nat Rev Mol Cell Biol, 2, 169-178). This control probe would further inform on whether observed labelling is consistent with a native E2-RING interaction, thus is suitable for screening inhibitors that disrupt the native interaction (FIG. 3e). Consistent with the probe being engaged in a native manner, the photoABP-UbBpa31 F62A probe did not undergo RING crosslinking. This should also serve as a valuable control probe when profiling RING E3s agnostically (FIG. 3f).

ABP Profiling of Poly-SUMO Chain Induced RNF4 Activation

Cellular RNF4 is activated by recruitment to poly-SUMO chains via its SIM domains thereby inducing dimerization. The $K_d$ of dimerization is ~180 Nm (Rojas-Fernandez et al., 2014, supra) thus, by working at concentrations below this value, we established a biochemical assay to assess whether photoABP-UbBpa31 could profile poly-SUMO chain-induced activation of native RNF4 (FIG. 3g). As expected, constitutively active RNF4-RING was insensitive to dilution and underwent photoABP-UbBpa31 crosslinking but native RNF4 did not (FIG. 3h). However, in the presence of a linear amide-linked tetra-SUMO (SUMOx4) fusion protein (10 µM), which recapitulates the activation properties of native isopeptide-linked polySUMO chains (Tatham et al., 2008, supra), photoABP-UbBpa31 crosslinking was observed with an efficiency comparable to that of RNF4-RING. Insightfully, a crosslinked band was observed for addition of a second photoABP-UbBpa31 molecule (FIG. 3g). This suggests that natively activated wild-type RNF4 retains its bipartite activity and its associated processivity is presumably utilized in cells. Taken together, the data so far demonstrate that photoABP-UbBpa31 undergoes activity-dependent crosslinking of a natively activated RING E3, which is devoid of a catalytic nucleophile.

Activity-Dependent Profiling Phosphorylation-Induced RING E3 Activation

PhotoABP-UbBpa31 was tested with a RING E3 that activates via a distinct mechanism. The Cbl proteins are multidomain and multifunctional RING E3 ligases consisting of three homologues: c-Cbl, Cbl-b and Cbl-c (Lyle, C. L., Belghasem, M., and Chitalia, V. C. (2019). Cells, 8). The majority of Cbl function is associated with RING E3 activity and involves regulation of angiogenesis. Aberrations in Cbl activity have been implicated with a number of cancers. Cbl is overexpressed in many breast cancer cells and tissues and is also found to be downregulated in myeloproliferative neoplasms (MDS/MPN) and non-small cell lung cancers (Kales, S. C. et al., (2010). Cancer Res, 70, 4789-4794; Tan, Y. H. et al., (2010). PLoS One, 5, e8972). Hence, modulation of Cbl E3 activity is an attractive therapeutic strategy and has attracted considerable interest from pharmaceutical companies. The most common mutation manifesting in the clinic is at residue Y371. Y371 is subject to phosphorylation by c-Src kinase and this leads to structural changes that present a non-RING element, enhance affinity for E2~Ub, and stimulate Cbl E3 activity (Buetow et al., 2016; Dou et al., 2013, supra). Indeed, the affinity for Cbl phosphorylated at Y371 (c-Cbl pTyr371) enhances E2~Ub affinity ~30-fold (Buetow et al., 2016, supra).

To assess whether photoABP-UbBpa31 can profile Src-dependent activation of c-Cbl E3 activity we incubated recombinant Src with Cbl and Cbl Y371F, the latter expected to be refractory to phosphorylation-induced activation. PhotoABP-UbBpa31 crosslinking was observed for c-Cbl in the presence of c-Src but not for c-Cbl Y371F, nor when c-Src was withheld (FIG. 4a). Labelling was again abolished with the photoABP-UbBpa31 F62A control probe (FIG. 11) and was also ATP-dependent (FIG. 12). Therefore, consistent with previous studies, phosphorylation at Y371 specifically is required for activation of E3 activity (Dou et al., 2013, supra). We also tested the panel of engineered E2~Ub conjugates with Bpa incorporation at different positions against c-Src activated c-Cbl and found partial overlap of productive sites with those for RNF4 (FIG. 13). An optimal Bpa position was 31 but unlike RNF4, position 32 (photoABP-UbBpa31) also crosslinked with similar efficiency. This is perhaps reflective of nuances between the monomeric and dimeric activation mechanism exhibited by these two RING E3s (Dou et al., 2013; Plechanovova et al., 2012, supra). Interestingly, photocrosslinking efficiency remained substoichiometric regardless of photoABP-UbBpa31 concentration suggestive of a subpopulation of the recombinant protein preparation being active (FIG. 14). Although Phostag gel analysis indicated that Cbl was quantitatively phosphorylated (FIG. 15), Src is known to phosphorylate multiple sites within Cbl and the degree of probe labeling may reflect substoichiometric phosphorylation at position Y371 (Dou, H. et al. (2012a). *Nat Struct Mol Biol,* 19, 184-192). We tested if incubation with elevated concentrations of Src could enhance photocrosslinking efficiency but found that as concentrations approached stoichiometry, photocrosslinking was inhibited; presumably due to Src competing against photoABP-UbBpa31 for Cbl binding (data not shown).

Profiling c-Cbl Activation in a Human Cell Line

To establish whether c-Cbl activation in a human cell line could be profiled, we transiently transfected human embryonic kidney cells (HEK293) cells with GST-tagged c-Src (GST-Src) together with GFP-tagged c-Cbl (GFP-Cbl) or GFP-tagged c-Cbl Y371F (GFP-Cbl Y371F). To prevent potential degradation of activated Cbl due to autoubiquitination we treated cells with the proteasome inhibitor MG132 for 90 minutes prior to lysis. Activity-dependent crosslinking was strictly dependent on Src coexpression and the presence of Y371 but absent with the photoE2~UbBpa31 F62A control probe (FIGS. 4b and 16). To afford the potential for future use in parallelized proteomic profiling of endogenous RING E3 ligases we prepared a biotinylated variant of photoABP-UbBpa31. Bpa was incorporated into N-terminal cysteine tagged Ub and labeled with idodoacetyl-PEG2-biotin. Biotin labelled UbBpa31 was then enzymatically conjugated to E2 via an isopeptide using the procedure for untagged Ub (FIG. 17).

Profiling Endogenous RING E3 Activation in Response to Growth Factor Stimulation We next assessed the ability to carry out parallelized profiling of endogenous RING E3 activation in response to a physiological stimulus. Such experiments would potentially enable poorly understood RING E3s to be ascribed to regulatory functions across a spectrum of both physiological and pathophysiological processes. Depletion of the ABP by promiscuous crosslinking might compromise RING E3 coverage and was initially tested for by immunoblotting against the hexahistidine reporter tag (FIG. 4c). Furthermore, crosslinking was substantially reduced with the photoABP-UbBpa31 F62A control probe, thereby implying that many of the crosslinked proteins are likely to be E3s (FIG. 4c).

We prepared a biotinylated variant of photoABP-UbBpa31 allowing selective enrichment of crosslinked proteins from complex cellular samples. Bpa was incorporated into N-terminal cysteine tagged Ub and labeled with iodoacetyl-PEG2-biotin (Pao et al., 2018, supra). Biotin labelled UbBpa31 was then enzymatically conjugated to E2 via an isopeptide using the procedure for untagged Ub (FIGS. 17 and 18). We next tested whether endogenous Cbl activation could be detected in response to EGF stimulation, which induces Cbl phosphorylation (Levkowitz et al., 1999; Levkowitz et al., 1998). HEK293T cells were stimulated with EGF and to prevent potential degradation of activated RING E3s, we prior treated with the proteasome and lysosomal inhibitors MG132 and bafilomycin, respectively. Parallel experiments confirmed EGF responsiveness by immunoblotting for downstream mitogen-activated protein (MAP) kinase activation, which is a robust marker of EGF-receptor activation (Traverse, S. et al. (1992). *Biochem. J.,* 288(Pt 2), 351-355, FIG. 19a).

Extracted proteomes were incubated with biotinylated photoABP-UbBpa31 and enriched against streptavidin resin (Pao et al., 2018, supra, FIG. 4d). Identification of crosslinked proteins and their probe reactivity was inferred by streptavidin enrichment followed by data-dependent liquid chromatography tandem mass spectrometry (LC-MS/MS) and spectral counting (Pao et al., 2018, supra). Twenty-five RING E3s were detected, including Cbl. Cbl peptides were only detected in EGF- and UV-treated samples (FIG. 4e). This suggests that the photocrosslinking probe can detect native RING E3 activation at the endogenous level. Interestingly, there was a notable increase in spectral counts for two other RING E3s, Praja2 and TRIM 11, that was EGF- and UV-dependent (FIG. 4e). As both of these E3s have been implicated with growth factor signaling, their detection may also be reflective of their activation or upregulation in response to EGF stimulation (Di, K. et al. (2013). *Oncogene,* 32, 5038-5047; Rinaldi, L. et al. (2016). *Cell Death Dis.* 7, e2230).

We unexpectedly obtained UV-dependent enrichment of HECT (11), RBR (1) and RCR (1) E3s, as well as deubiquitinating enzymes (DUBs) (31) and an E1 activating enzyme (FIGS. 19a and 19b). As a consequence, probe modification of these additional ubiquitin system components could modulate their activity and alter the activation status, or stability, of RING E3s under investigation. However, this is unlikely to pose any limitations beyond those associated with the employment of cellular extracts where the majority of cellular processes would be arrested.

Production of Photocrosslinking ABP Based on an Alternative E2

An ABP based on a different E2 enzyme has also been synthesized. The enzyme UBE2N (also known as Ubc13) was employed. To conjugate the Bpa31 mutant Ub molecule to the active site position, a similar strategy was employed as described above. The catalytic cysteine (Cys87) was mutated to lysine, allowing stable E1-mediated isopeptide conjugation. It should be noted that, in other work employing wild type ubiquitin, conjugation to a native lysine residue in proximity of the active site was observed (Lys92) (Branigan, et al. *Nat Struct Mol Biol* 22, 597-602). Thus, to ensure homogenous modification, a UBE2N C87K K92A double mutant was employed as exemplified in the Branigan et al. study. The UBE2N probe was functional with an E3 ligase (TRAF6) known to be a physiological partner of the UBE2N E2 enzyme (FIG. 20). A probe based on UBE2N where the ubiquitin molecule has been biotinylated, as described above for UBE2D3, has also been prepared (Ubc13-Biotin-UbBpa3) and shown to be capable of activity-based proteomic profiling of RING E3 ligases in cellular extracts.

Discussion

In summary, we have developed activity-based probes for the adapter-like activity of RING E3 ligases. We demonstrate an activity-dependent signal for RNF4, c-Cbl and TRAF6 in response to their native activation cues and how the ABP-based readout can afford further mechanistic insights. These tools allow direct assessment of RING E3 activity (no dependence on E1, E2, or substrate) in diverse sample types. We also demonstrate parallelized profiling of a subset of endogenous RING E3s in extracted proteomes and detect activation of Cbl in response to growth factor stimulation. As such, this technology should find utility in the study of RING E3 regulatory biology, target discovery, biomarker applications and modulator discovery. Detection of only a subset of RING E3s in our LC-MS/MS experiments might be reflective of many being inactive or beyond the detection limit of our current experimental conditions. Another possibility is that many E3s are not functional with the E2 enzyme used (photoABP-UbBpa31 is based on (UBE2D3)). However, the engineered isopeptide conjugation strategy, for stabilizing the labile thioester, has been demonstrated with E2s that are divergent from UBE2D3, such as UBE2N (Branigan et al., 2015; Ordureau et al., 2015). Hence, our highly modular probe production strategy should be readily applicable to other E2s simply by using distinct recombinant E2 building blocks. This would potentially grant broader RING E3 coverage and also provide insights into cellular E2-E3 interaction networks.

The invention claimed is:

1. A conjugate molecule comprising an activated ubiquitin molecule of SEQ ID NO: 1 comprising a photocrosslinker moiety in place of a glutamine residue at position 31 and/or aspartic acid residue at position 32 of ubiquitin conjugated to an E2 conjugating enzyme.

2. The conjugate molecule according to claim 1, wherein the E2 conjugating enzyme is a mutant enzyme comprising a C85K or C87K mutation and/or an S22R or K92A mutation.

3. The conjugate molecule according to claim 1, wherein the E2 conjugating enzyme is UBE2D3 or UBE2N.

4. The conjugate molecule according to claim 1, further comprising an N-terminal His-tag group.

5. A method of profiling the activity of RING E3 enzymes, E1 enzymes and/or deubiquitinating enzymes, the method comprising contacting the conjugate molecule according to claim 1 with said RING E3 enzymes, E1 enzymes and/or deubiquitinating enzymes and detecting formation of any new conjugates.

6. The method according to claim 5, wherein activity profiling is of a RING E3 enzyme.

7. The method according to claim 6 for (i) the study of RING E3 enzyme regulation, (ii) discovery of novel RING E3 enzymes, (iii) inhibitor screening, (iv) inhibitor selectivity profiling; and/or (v) stabilization of enzymatic intermediates for structural studies.

8. A method of detecting an interaction between the conjugate molecule of claim 1 and a RING E3 enzyme, E1 enzyme and/or deubiquitinating enzyme, the method comprising contacting the conjugate molecule with said RING E3 enzyme, E1 enzyme and/or deubiquitinating enzyme and detecting formation of any new conjugates.

9. The method of claim 8, wherein the RING E3 enzyme is any one or a combination of RNF4, Cbl, Praja2, TRIM11, HECT, RBR, RCR, TRAF6, TRAF2 and HLTF.

10. The method of claim 8, wherein interaction is with a RING E3 enzyme.

11. The conjugate molecule according to claim 1, wherein the ubiquitin is human ubiquitin.

12. The conjugate molecule according to claim 1, wherein the photocrosslinker moiety has been obtained by incorporation of an unnatural amino acid, optionally p-benzoyl-L-phenylalanine, in place of the aspartic acid/glutamine residue.

13. The conjugate molecule according to claim 1, wherein the activated ubiquitin molecule further comprises a reporter tag.

14. The conjugate molecule according to claim 13, wherein the reporter tag is a biotin moiety, or other reporter allowing analytical detection.

15. The conjugate molecule according to claim 14, wherein the reporter tag is an epitope tag or a fluorophore.

16. The conjugate molecule according to claim 13, wherein the reporter tag is covalently attached to the ubiquitin molecule by way of a linker molecule attached to the N-terminus of the ubiquitin.

17. The conjugate molecule according to claim 4, wherein the N-terminal His-tag group is a hexahistidine tag.

18. The method according to claim 9, wherein Cbl is c-Cbl.

\* \* \* \* \*